US008426575B2

(12) United States Patent
Borca et al.

(10) Patent No.: US 8,426,575 B2
(45) Date of Patent: Apr. 23, 2013

(54) N-LINKED GLYCOSYLATION ALTERATION IN E1 GLYCOPROTEIN OF CLASSICAL SWINE FEVER VIRUS AND NOVEL CLASSICAL SWINE FEVER VIRUS VACCINE

(75) Inventors: Manuel V. Borca, Westbrook, CT (US); Guillermo R. Risatti, Westbrook, CT (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/238,919

(22) Filed: Sep. 21, 2011

(65) Prior Publication Data

US 2012/0014992 A1    Jan. 19, 2012

Related U.S. Application Data

(62) Division of application No. 12/008,958, filed on Jan. 15, 2008, now Pat. No. 8,114,852.

(51) Int. Cl.
*A61K 39/12* (2006.01)
*A61K 38/00* (2006.01)

(52) U.S. Cl.
USPC ............... 536/23.72; 424/186.1; 435/235.1

(58) Field of Classification Search .................. None
See application file for complete search history.

(56) References Cited

PUBLICATIONS

Yasuhiro, A., et al., "Effect of the Addition of Oligosaccharides on the Biological Activities and Atigenicity of Influenza A/H3N2 Virus Hemagglutinin", J. of Virology, vol. 78, (18), 2004, pp. 9605-9611.
Deshpande, K., et al., "Glycosylation Affects Cleavage o fan H5N2 Influenza Virus Hemagglutinin and Regulates Virulence", Proceedings of the National Academy of Sciences, vol. 84, 1987. pp. 36-40.
Horimoto, T., et al., "Reverse Genetics Provides Direct Evidence for a Correlation of Hemagglutinin Cleavability and Virulence of an Avian Influenza A Virus", J. of Virology, vol. 68, (5), 1994, pp. 3120-3128.
Hulse, D., et al., "Molecular Determinants within the Surface Proteins Involved in the Pathogenicity of H5N1 Influenza Viruses in Chickens", J. of Virology, vol. 78, (18), 2004, pp. 9954-9964.
Moormann, R., et al., "Nucleotide Sequence of Hog Cholera Virus RNA Properties of the Polyprotein Encoded by the Open Reading Frame Spanning the Viral Genomic RNA", Veterinary Microbiology, vol. 23, 1990, pp. 185-191.
Meyers, G., et al., "Mutations Abrogating the RNase Activity in Glycoprotein Ems of the Pestivirus Classical Swine Fever Virus Lead to Virus Attenuation", J. of Virology, vol. 73, (12), 1999, pp. 10224-10235.
Panda, A., et al., "Loss of N-Linked Glycosylation from the Hemagglutinin-Neuraminidase Protein Alters Virulence of Newcastle Disease Virus", J. of Virology, vol. 78, (10), 2004, pp. 4965-4975.
Risatti, G., et al., "N-Linked Glycosylation Status of Classical Swine Fever Virus Strain Brescia E2 Glycoprotein Influences Virulence in Swine", J. of Virology, vol. 81, (2), 2007, pp. 924-933.
Risatti, G., et al., "Identification of a Novel Virulence Determinant within the E2 Structural Glycoprotein of Classical Swine Fever Virus", Virology, vol. 355, 2006, pp. 94-101.
Risatti, G., et al., "Mutation of E1 Glycoprotein of Classical Swine Fever Virus Affects Viral virulence in Swine". Virology, vol. 343, 2005, pp. 116-127.
Risatti, G., et al., "The E2 Glycoprotein of Classical Swine Fever Virus is a Virulence Determinant in Swine", J. of Virology, vol. 79, (6), 2005, pp. 3787-3796.
Fernando Sainz, I., et al., "Removal of a N-Linked Glycosylation Site of Classical Swine Fever Virus Strain Brescia Ems Glycoprotein Affects Virulence in Swine", Virology, vol. 370, 2008, pp. 122-129.
Thiel, H., et al., "Hog Cholera Virus: Molecular Composition of Virions from a Pestivirus", J. of Virology, vol. 65, (9), 1991, pp. 4705-4712.
Van Gennip, H., et al., "Determinants of Virulence of Classical Swine Fever Virus Strain Brescia", J. of Virology, vol. 78, (16), 2004, pp. 8812-8823.

*Primary Examiner* — Bao Li
(74) *Attorney, Agent, or Firm* — John D. Fado; Evelyn M. Rabin; Robert D. Jones

(57) ABSTRACT

E1, along with Erns and E2 is one of the three envelope glycoproteins of Classical Swine Fever Virus (CSFV). Our previous studies indicated that glycosylation status of either E2 or Erns strongly influence viral virulence in swine. Here, we have investigated the role of E1 glycosylation of highly virulent CSFV strain Brescia during infection in the natural host. The three putative glycosylation sites in E1 were modified by site directed mutagenesis of a CSFV Brescia infectious clone (BICv). A panel of virus mutants was obtained and used to investigate whether the removal of putative glycosylation sites in the E1 glycoprotein would affect viral virulence/pathogenesis in swine. We observed that rescue of viable virus was completely impaired by removal of all three putative glycosylation sites in E1. Single mutations of each of the E1 glycosylation sites showed that CSFV amino acid N594 (E1.N3 virus), as well the combined mutation of N500 and N513 (E1.N1N2 virus) resulted in BICv attenuation. Infection of either E1.N1N2 or E1.N3 viruses were able to efficiently protected swine from challenge with virulent BICv at 3 and 28 days post-infection. These results, along with those demonstrating the role of glycosylation of $E^{rns}$ and E2, suggest that manipulation of the pattern of glycosylation could be a useful tool for development of CSF live-attenuated vaccines.

13 Claims, 6 Drawing Sheets
(1 of 6 Drawing Sheet(s) Filed in Color)

|  |  | N1 N2 | N3 | | Relative virus yield |
|---|---|---|---|---|---|
| BICv | E0 | YY | Y | E1 ... E2 | 1.00 |
| E1.N1v |  | ΔY | Y |  | 0.86 |
| E1.N2v |  | YΔ | Y |  | 0.89 |
| E1.N3v |  | YY | Δ |  | 0.80 |
| E1.N1N2N3v |  | ΔΔ | Δ |  | Non viable |
| E1.N1N2v |  | ΔΔ | Y |  | 0.83 |
| E1.N1N3v |  | Y | Δ |  | Non viable |
| E1.N2N3v |  | YΔ | Δ |  | Non viable |

N-LINKED GLYCOSYLATION ALTERATION IN E1 GLYCOPROTEIN OF CLASSICAL SWINE FEVER VIRUS AND NOVEL CLASSICAL SWINE FEVER VIRUS VACCINE

This application is a divisional application of application Ser. No. 12/008,958, filed Jan. 15, 2008, now pending, which is herein incorporated by reference in its entirety.

BACKGROUND OF THE INVENTION

1. Field of the Invention

This invention relates to the characterization of the role that glycosylation of the transmembrane glycoprotein E1 of highly virulent Classical Swine Fever Virus (CSFV) strain Brescia plays during infection in the natural host and to the utilization of a strategy for manipulating the pattern of glycosylation for particular E1 glycosylation sites in order to alter CSFV virulence, providing a useful tool in the design and development of CSF live-attenuated vaccines.

2. Description of the Relevant Art

Classical swine fever (CSF) is a highly contagious disease of swine. The etiological agent, CSF virus (CSFV), is a small, enveloped virus with a positive, single-stranded RNA genome and, along with Bovine Viral Diarrhea Virus (BVDV) and Border Disease Virus (BDV), is classified as a member of the genus Pestivirus within the family Flaviridae (Becher et al. 2003. *Virology* 311: 96-104). The 12.5 kb CSFV genome contains a single open reading frame that encodes a 3898-amino-acid polyprotein and ultimately yields 11 to 12 final cleavage products ($NH_2$-Npro-C-$E^{rns}$-E1-E2-p7-NS2-NS3-NS4A-NS4B-NS5A-NS5B-COOH) through co- and post-translational processing of the polyprotein by cellular and viral proteases (Rice, C. M. 1996. In: *Fundamental Virology*, 3rd edition, Knipe et al., eds., Lippincott Raven, Philadelphia, Pa., pages 931-959). Structural components of the CSFV virion include the capsid (C) protein and glycoproteins $E^{rns}$, E1, and E2. E1 and E2 are anchored to the envelope at their carboxyl termini and Erns loosely associates with the viral envelope (Slater-Handshy et al. 2004. *Virology* 319: 36-48; Weiland et al. 1990. *J. Virol.* 64: 3563-3569; Weiland et al. 1999. *J. Gen. Virol.* 80: 1157-1165). E1 and E2 are type I transmembrane proteins with an N-terminal ectodomain and a C-terminal hydrophobic anchor (Thiel et al. 1991. *J. Virol.* 65: 4705-4712). E1 has been implicated (Wang et al. 2004. *Virology* 330: 332-341), along with $E^{rns}$ and E2 (Hulst et al. 1997. *J. Gen Virol.* 78: 2779-2787), in viral adsorption to host cells. Importantly, modifications introduced into these glycoproteins appear to have an important effect on CSFV virulence (Meyers et al. 1999. *J. Virol.* 73: 10224-10235; Risatti et al. 2005a. *J. Virol.* 79: 3787-3796; Risatti et al. 2005. *Virology* 355: 94-101; Risatti et al. 2005b. *Virology* 343; 116-127; Van Gennip et al. 2004. *J. Virol.* 78: 8812-8823).

Glycosylation is one of the most common types of protein modifications. N-linked oligosaccharides are added to specific asparagine residues in the context of the consensus sequence Asn-X-Ser/Thr (Kornfeld and Kornfeld 1985. *Annu. Rev. Biochem.* 54: 631-664). According to a glycosylation analysis algorithm (Retrieved from the Internet: <URL: cbs.dtu.dk/services/), E1 of the CSFV strain Brescia has three putative N-linked glycosylation sites although this is not confirmed by experimental evidence. Predicted E1 glycosylation sites (at CSFV amino acid residue position N500, N513 and N594) are highly conserved among CSFV isolates and two of them (N513 and N594) are also conserved in other Pestiviruses. However, the significance of viral envelope protein glycosylation in virus replication, pathogenesis, and virulence in the natural host is not completely defined. It has just been recently described that specific removal of certain putative glycosylation sites in $E^{rns}$ and E2 significantly alters the virulence of highly virulent Brescia strain in swine (Fernandez Sainz et al., 2008. *Virology* (370:122-129); Risatti et al., 2007. *J. Virol.* 81: 924-933).

Strategies for controlling disease in the event of a CSFV outbreak include the production of rationally designed live attenuated vaccine CSFV strains. Thus, the effect of modification of glycosylation sites of other of the CSFV virion glycoproteins need to be evaluated. Here, we report the effects of modification of particular predicted E1 glycosylation sites. We used oligonucleotide site-directed mutagenesis of the E1 gene of the highly virulent CSFV strain Brescia to construct a panel of glycosylation mutants. These mutants were evaluated to determine whether the removal of each of these glycosylation sites in the E1 glycoprotein could affect viral infectivity and virulence in swine.

SUMMARY OF THE INVENTION

We have discovered glycosylation sites within the classical swine fever virus (CSFV) E1 glycoprotein where modification of the sites results in CSFV having novel virulence determinants.

In accordance with this discovery, it is an object of the invention to provide a recombinant CSFV comprising DNA encoding a modified CSFV E1 glycoprotein wherein specific glycosylation sites within E1 have been mutated resulting in an alteration in the site, i.e., the formerly glycosylated amino acid being altered and replaced by a non-glycosylated amino acid.

It is also an object of the invention to provide an isolated polynucleotide molecule comprising a genetically modified DNA sequence encoding a genetically modified infectious RNA molecule encoding a genetically modified CSFV. The CSFV is genetically modified such that when it infects a porcine animal it is unable to produce CSFV in the animal and it is able to elicit an effective immunoprotective response against infection by a CSFV in the animal. Mutated sequences or sequences homologous thereto contain a mutation that renders the encoded CSFV attenuated and able to elicit an effective immunoprotective response against infection by a CSFV in the animal.

It is additionally an object of the invention to provide an isolated infectious RNA molecule encoded by the isolated polynucleotide molecule recited above, and isolated infectious RNA molecules homologous thereto, which isolated infectious RNA molecules each encode a genetically modified CSFV, disabled in its ability to produce CSF.

An added object of the invention is to provide immunogenic compositions comprising a viable recombinant CSFV comprising a modified CSFV E1 glycoprotein displaying a glycosylation pattern different from that of the non-mutated E1 glycoprotein.

An additional object of the invention is to provide a rationally designed live attenuated CSFV vaccine which lessens severity of CSF disease when challenged with virulent Brescia CSFV wherein said vaccine comprises an altered glycosylation pattern as compared to that of the infectious, non-mutated virus.

Another object of the invention is to provide a rationally designed live attenuated CSFV vaccine effective to protect an animal from clinical CSF disease when challenged with virulent Brescia CSFV wherein said vaccine comprises an altered glycosylation pattern as compared to that of the infectious, non-mutated virus.

A further object of the invention is to provide a marker vaccine which allows a serological distinction between vaccinated animals and animals infected with CSFV.

A still further object of the invention is to provide a method for making a genetically modified CSFV, which method comprises mutating an infectious cDNA sequence, transforming the modified DNA into a modified infectious RNA molecule encoding a modified CSFV, and rescuing the genetically modified CSFV there from subsequent to said mutation.

Yet another object of the invention is to provide a method for protecting an animal against CSF by administering an effective amount of rationally designed live attenuated CSFV vaccine.

An additional object of the invention is to provide a method for delaying onset or severity of CSF in an animal by administering an effective amount of rationally designed live attenuated CSFV vaccine.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

Figure 1B:
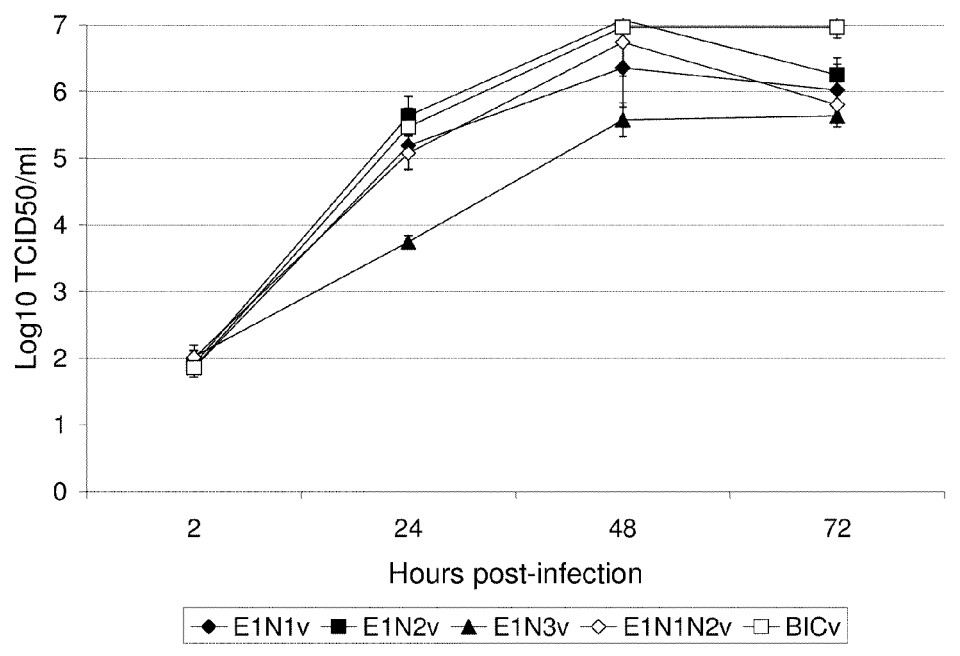

FIG. 1A is a schematic representation of glycosylation mutants of Classical Swine Fever Virus E1 protein, generated by site-directed mutagenesis of a cDNA full-length clone pBIC (Terpstra et al. 1990. *Dtsch Tierarztl Wochenschr* 97: 77-79). Wild type E1 glycoprotein shown at the top. Y: putative glycosylation sites. Mutants were named with an N (N-linked glycosylation) followed by a number that represents the relative position of putative glycosylation sites within E1 amino acid sequence (500, 513, 594). Relative virus yield is final point virus yield as proportion of final end point (72 hours post-infection) virus yield of parental BICv. FIG. 1B shows the in vitro growth characteristics of E1 glycosylation mutants and parental BICv. Primary swine macrophage cell cultures were infected (MOI=0.01) with each of the mutants or BICv and virus yield was titrated at times post infection in SK6 cells. Data represent means and standard deviations from two independent experiments. Sensitivity of virus detection: >1.8 $TCID_{50}$/ml.

DETAILED DESCRIPTION OF THE INVENTION

Figure 1C:
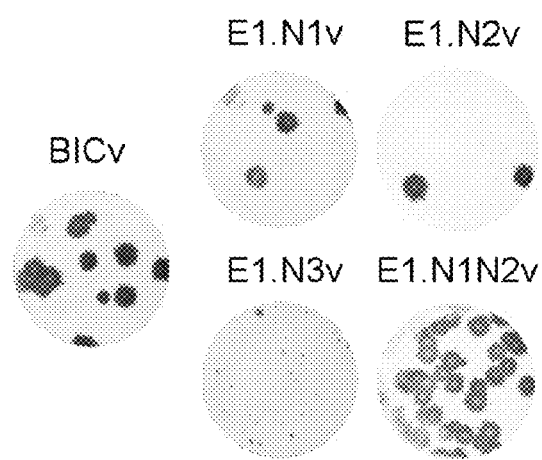
FIG. 1C shows plaque formation of E1 glycosylation mutants and BICv. SK6 monolayers were infected, overlaid with 0.5% agarose and incubated at 37° C. for 3 days. Plates were fixed with 50% (vol/vol) ethanol-acetone and stained by immunohistochemistry with mAb WH303.
Figure 2A:
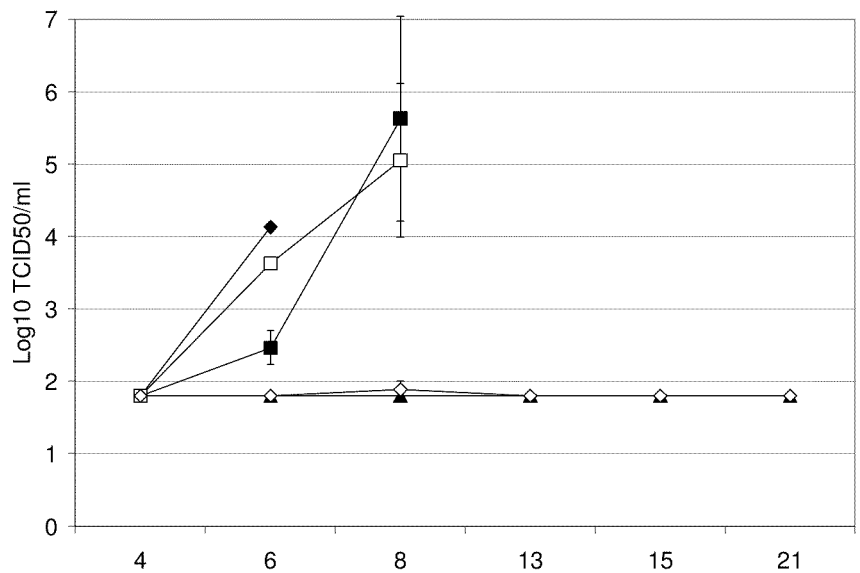
FIGS. 2A, 2B, and 2C depict the virus titers and FIGS. 2D and 2E, the hematological data, in nasal swabs, tonsil scrapings, and blood from animals infected with CSFV E1 glycosylation mutants or parental BICv. Peripheral white blood cell and platelet counts are expressed as numbers/ul of blood. Data represent means and standard deviations from at least two animals. Sensitivity of virus detection: >1.8 $TCID_{50}$/ml.
Figure 2B:
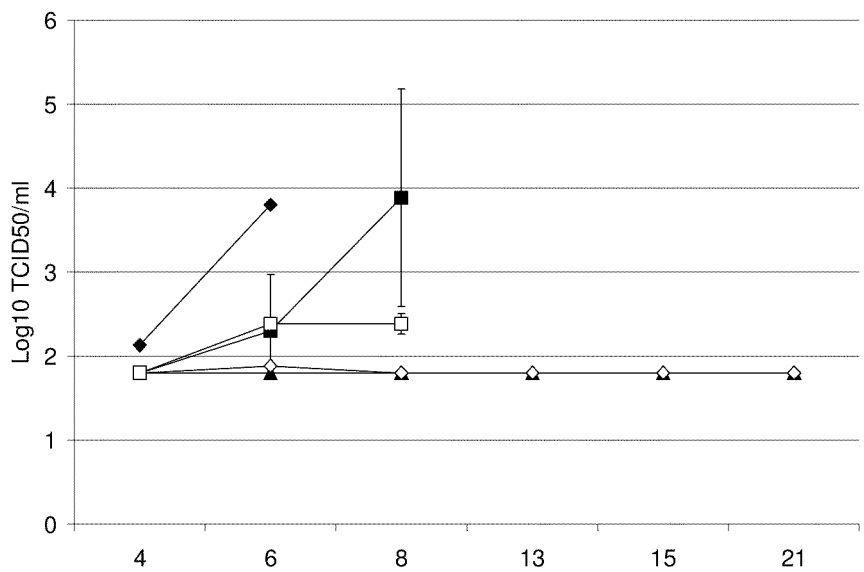
Figure 2D:
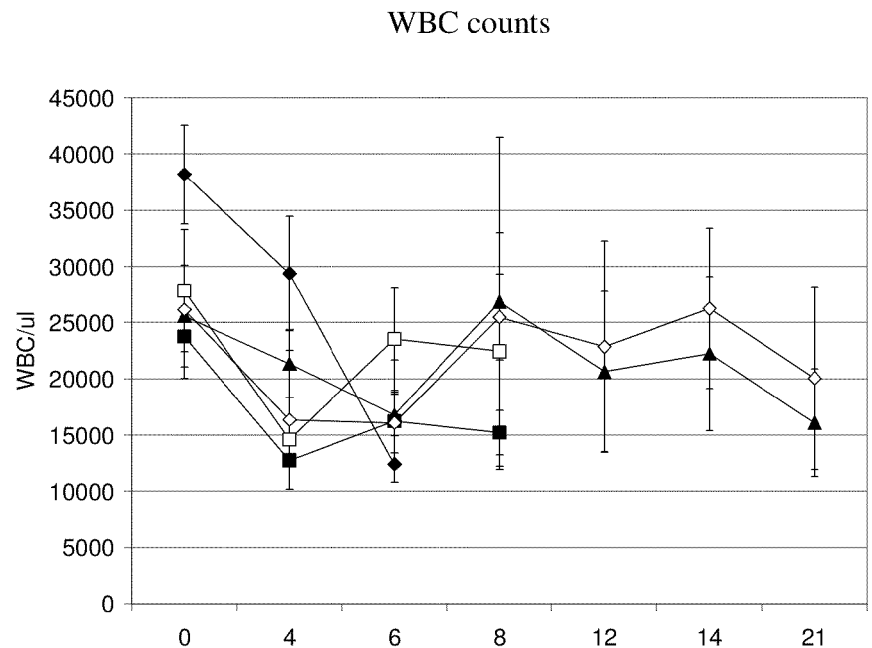
Figure 2E:
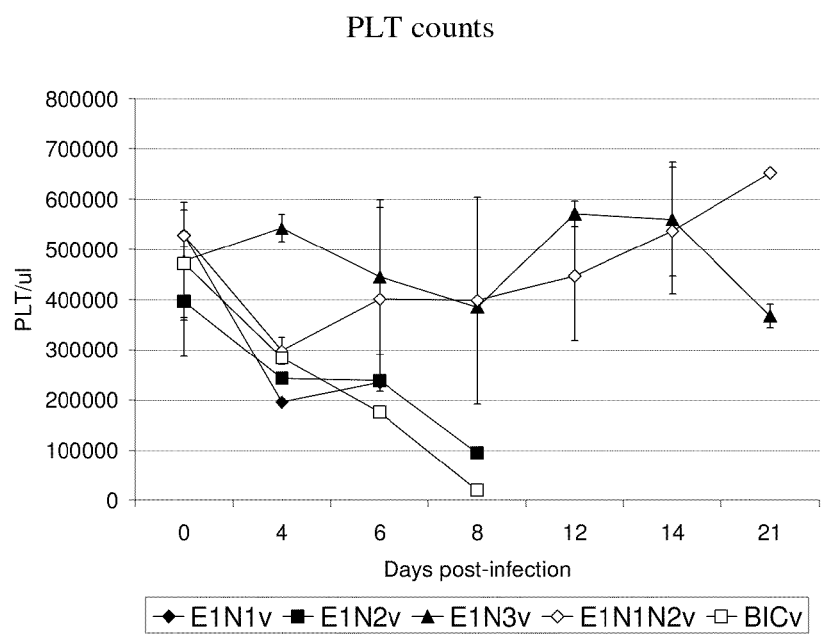

Virus glycoproteins are crucial in key steps of the virus cycle such as attachment to host cell receptors, entry, assembly of newly produced viral progeny, and exit. In vivo viral glycoproteins have been shown to influence infectivity (Ansari et al. 2006. *J. Virol.* 80: 3994-4004), virulence (Hulse et al. 2004. *J. Virol.* 78: 9954-9984; Panda et al. 2004. *J. Virol.* 78: 4965-4975), and host immune response (Abe at al. 2004. *J. Virol.* 78: 9605-9611). Added oligosaccharides confer proper function to viral glycoproteins since alteration of those glycosylation sites have shown dramatic consequences for viruses affecting protein folding (Herbert at al. 1997. *J. Cell Biol.* 139: 613-623; Kornfeld, supra; Shi et al. 2005. *J. Virol.* 79: 13725-13734; Shi and Elliott. 2004. *J. Virol.* 78: 5414-5422; Slater-Handshy, supra) and protein active conformation (Meunier at al. 1999. *J. Gen. Viral.* 80: 887-896). In this study, we analyzed glycosylation of the CSFV E1 glycoprotein and evaluated its effect on the virulence of CSFV in swine. DNA encoding CSFV strain Brescia E1 glycoprotein contains 3 N-linked putative glycosylation sites (Retrieved from the Internet: <URL: obs.dtu.dk/services/) ((Moorman et al. 1990. *Vet. Microbiol.* 23: 185-191). Sequence analysis of CSFV E1 glycoprotein showed that 3 of the N-linked glycosylation sites are highly conserved in CSV strains CSFV and two of them (N513 and N594) also among BVDV type and II, and BDV strains (data not shown), implying an important role for these sites in all Pestiviruses. However, very little is known about the role of glycosylation on the function of Pestivirus glycoproteins. All putative glycosylation sites in E1 were modified by site-directed mutagenesis using a full-length cDNA infectious clone of virulent strain Brescia as the target sequence. Here, we showed that some of these sites have a major role in virulence and protection; some of the sites seem to be critical for the production of viable virus.

Cleavage and glycosylation patterns of the hemagglutinin gene of H5 avian influenza viruses have been shown to affect pathogenicity in chickens (Deshpande et al. 1987. *Proc. Natl. Acad. Sci. USA* 84: 36-40; Horimoto and Kawaoka. 1994. *J. Virol.* 68: 3120-3128). More recently it has been shown that glycosylation patterns of the neuraminidase gene of highly pathogenic H5N1 avian flu viruses are important for increased virulence in chickens (Hulse, supra). The mechanisms by which these patterns affect avian flu virulence are unknown. Similarly, a single mutation (E1.N3v) or multiple mutations (E1.N1N2v) within E1 resulted in attenuated viruses with restricted in vivo replication ability (see Table 2). Unlike the acute fatal disease induced by BICv, infections caused by these mutants were sub-clinical in swine and characterized by decreased viral replication in target organs and reduced virus shedding. Interestingly, mutants E1.N1v, and E1.N2v retained the same capability of causing severe disease in swine as parental BICv, showing that in vivo E1 functions are retained and not influenced by the lack of glycans at positions N500 and N513. As with avian flu, the genetic basis and the molecular mechanisms underlying CSFV virulence remain unknown.

As shown in this study, single mutations of E1 putative glycosylation sites have no effect on in vitro or in vivo infectivity of CSFV, with the exception of residue N594 in the E1.N3v mutant. However, when multiple site mutations were introduced in E1, we observed that any multiple mutations involving residue N594 (E1.N1N2, E1.N1N3 or E1.N1N2N3) render non-viable viruses (data not shown).

Production and manipulation of the isolated polynucleotide molecules described herein are within the skill in the art and can be carried out according to recombinant techniques described, among other places, in Sambrook et al. 1989. *Molecular Cloning: A Laboratory Manual,* 2d ed., Cold Spring Harbor Laboratory Press, Cold Spring Harbor, N.Y. and Innis et al. (eds). 1995. *PCR Strategies,* Academic Press, Inc., San Diego, which are incorporated herein by reference.

The subject invention provides isolated polynucleotide molecules comprising genetically modified DNA sequences that encode genetically modified infectious RNA molecules that encode genetically modified Classical Swine Fever Viruses (CSFVs).

In particular, the subject invention provides an isolated polynucleotide molecule comprising a genetically modified DNA sequence encoding a genetically modified infectious RNA molecule that encodes a genetically modified CSFV, wherein said DNA sequences are SEQ ID NO:1 (E1.N1N2) and SEQ ID NO:3 (E1.N3) or sequences homologous thereto encoding the mutated viruses. Said DNA sequences encode infectious RNA molecules that are the RNA genomes of the mutated CSF viruses E1.N1N2 and E1.N3, respectively.

It is understood that terms herein referring to nucleic acid molecules such as "isolated polynucleotide molecule" and "nucleotide sequence include both DNA and RNA molecules and include both single-stranded and double-stranded molecules whether it is natural or synthetic origin.

For example, SEQ ID NO:1 is a DNA sequence corresponding to the genetically modified RNA genome of a genetically modified CSFV. Thus, a DNA sequence complementary to the DNA sequence set forth in SEQ ID NO:1 is a template for, i.e. is complementary to or "encodes", the RNA genome of the SF virus (i.e., RNA that encodes the CSFV).

Furthermore, when reference is made herein to sequences homologous to a sequence in the Sequence Listing, it is to be understood that sequences are homologous to a sequence corresponding to the sequence in the Sequence Listing and to a sequence complementary to the sequence in the Sequence Listing.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a modified CSFV E1 glycopeptide (E1.N1N2 or E1.N3) and which hybridize under stringent conditions, as described herein, to the modified CSFV E1 sequences disclosed herein, i.e., SEQ ID NO:1 (E1.N1N2) or SEQ ID NO:3 (E1.N3) or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.*

85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of one of the CSFV E1 glycoproteins of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, a modified CSFV E1 glycoprotein activity, i.e., E1.N1N2 or E1.N3 glycoprotein activity as described herein. Such variants may result from, for example, genetic polymorphism or from human manipulation. Biologically active variants of a modified CSFV E1 glycoprotein of the invention, i.e., E1.N1N2 or E1.N3, will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified CSFV E1 glycoprotein activity, i.e., E1.N1N2 or E1.N3 glycoprotein activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of modified CSFV E1 glycoprotein, i.e., E1.N1N2 or E1.N3 glycoprotein activity, can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "CSF" encompasses disease symptoms in swine caused by a CSFV infection. Examples of such symptoms include, but are not limited to, anorexia, depression, fever, purple skin discoloration, staggering gait, diarrhea and cough. As used herein, a CSFV that is "unable to produce CSF" refers to a virus that can infect a pig, but which does not produce any disease symptoms normally associated with a CSF infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The terms "classical swine fever virus" and "CSFV", as used herein, unless otherwise indicated, mean any strain of CSF viruses.

The term "open reading frame", or "ORF", as used herein, means the minimal nucleotide sequence required to encode a particular CSFV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine cells, and are described in further detail below.

A "functional virion" is a virus particle that is able to enter a cell capable of hosting a CSFV, and express genes of its particular RNA genome (either an unmodified genome or a genetically modified genome as described herein) within the cell. Cells capable of hosting a CSFV include swine kidney cells (SK6) and primary porcine macrophage cell cultures. Other mammalian cells, especially other porcine cells, may also serve as suitable host cells for CSF virions.

The isolated polynucleotide molecules of the present invention encode CSF viruses that can be used to prepare live attenuated vaccines using art-recognized methods for protecting swine from infection by a CSFV, as described in further detail below. Furthermore, these isolated polynucleotide molecules are useful because they can be mutated using molecular biology techniques to encode genetically-modified CSF viruses useful, inter alia, as vaccines for protecting swine from CSF infection. Such genetically-modified CSF viruses, as well as vaccines comprising them, are described in further detail below.

Accordingly, the subject invention further provides a method for making a genetically modified CSFV, which method comprises mutating the DNA sequence encoding an infectious RNA molecule which encodes the CSFV as described above, and expressing the genetically modified CSFV using a suitable expression system. A CSFV, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art.

The subject invention further provides an isolated polynucleotide molecule comprising a DNA sequence encoding an infectious RNA molecule which encodes a genetically modified CSFV that is unable to produce CSF in a porcine animal, wherein the DNA sequence encoding the infectious RNA molecule encoding said modified CSFV is SEQ ID NO:1 or SEQ ID NO:3 or a sequences homologous thereto, contains one or more mutations that genetically disable the encoded CSFV in its ability to produce CSF. "Genetically disabled" means that the CSFV is unable to produce CSF in a swine animal infected therewith.

In one embodiment, the genetically modified CSFV disabled in its ability to cause CSF is able to elicit an effective immunoprotective response against infection by a CSFV in a swine animal. Accordingly, the subject invention also provides an isolated polynucleotide molecule comprising a DNA sequence encoding an infectious RNA molecule which encodes a CSFV that is genetically modified such that when it infects a porcine animal it: a) is unable to produce CSF in the animal, and b) is able to elicit an effective immunoprotective response against infection by a CSFV in the animal, wherein the DNA sequence encoding said modified CSFV is SEQ ID NO:1 (E1.N1N2) or SEQ ID NO:3 (E1.N3) or sequences homologous thereto, contains one or more mutations that genetically disable the encoded CSFV in its ability to produce CSF.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polypeptide sequences, optionally comprising non-protein groups such as carbohydrate moieties and/or lipid moieties.

The genetically modified CSF viruses encoded by the above-described isolated polynucleotide molecules are, in one embodiment, able to elicit an effective immunoprotective response against infection by a CSFV. Such genetically modified CSF viruses are preferably able to elicit an effective immunoprotective response against any strain of CSF viruses.

In one embodiment, the mutation or mutations in the isolated polynucleotide molecule encoding the genetically disabled CSFV are non-silent and occur in one or more open reading frames of the nucleotide sequence encoding the CSFV.

As used herein, unless otherwise indicated, "coding regions" refer to those sequences of RNA from which CSFV proteins are expressed, and also refer to cDNA that encodes such RNA sequences. Likewise, "ORFs" refer both to RNA sequences that encode CSFV proteins and to cDNA sequence encoding such RNA sequences.

Determining suitable locations for a mutation or mutations that will encode a CSFV that is genetically disabled so that it is unable to produce CSF yet remains able to elicit an effective immunoprotective response against infection by a CSFV can be made based on SEQ ID NO:1 and SEQ ID NO:3 provided herein. One of ordinary skill can refer to the sequence of the infectious cDNA clone of CSFV provided by this invention, make sequence changes which will result in a mutation altering the glycosylation pattern of the glycoprotein, and test the viruses encoded thereby both for their ability to produce CSF in swine, and to elicit an effective immunoprotective response against infection by a CSFV. In so doing, one of ordinary skill can refer to techniques known in the art and also those described and/or exemplified herein.

For example, an ORF of the sequence encoding the infectious RNA molecule encoding the CSFV can be mutated and the resulting genetically modified CSFV tested for its ability to cause CSF.

In a further preferred embodiment, an antigenic epitope of the genetically modified CSFV of the present invention is a detectable antigenic epitope. Such isolated polynucleotide molecules and the CSF viruses they encode are useful, inter alia, for studying CSF infections in swine, determining successfully vaccinated swine, and/or for distinguishing vaccinated swine from swine infected by a wild-type CSFV. Preferably, such isolated polynucleotide molecules further contain one or more mutations that genetically disable the encoded CSFV in its ability to produce CSF, and more preferably are able to elicit an effective immunoprotective response in a porcine animal against infection by a CSFV.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

The present invention further provides an isolated polynucleotide molecule comprising a DNA sequence encoding an infectious RNA molecule which encodes a genetically modified CSFV that detectably lacks a CSFV antigenic epitope, wherein the DNA sequence encoding the RNA molecule encoding the modified CSFV is SEQ ID NO:1 (E1.N1.N2) or SEQ ID NO:3 (E1.N3) or sequences homologous thereto, except that it lacks one or more nucleotide sequences encoding a detectable CSFV antigenic epitope. Such isolated polynucleotide molecules are useful for distinguishing between swine infected with a recombinant CSFV of the present invention and swine infected with a wild-type CSFV. For example, animals vaccinated with killed, live or attenuated CSFV encoded by such an isolated polynucleotide molecule can be distinguished from animals infected with wild-type CSF based on the absence of antibodies specific to the missing antigenic epitope, or based on the absence of the antigenic epitope itself. If antibodies specific to the missing antigenic epitope, or if the antigenic epitope itself, are detected in the animal, then the animal was exposed to and infected by a wild-type CSFV. Means for detecting antigenic epitopes and antibodies specific thereto are known in the art, as discussed above. Preferably, such an isolated polynucleotide molecule further contains one or more mutations that genetically disable the encoded CSFV in its ability to produce CSF. More preferably, the encoded virus remains able to elicit an effective immunoprotective response against infection by a CSFV.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., *Remington's Pharmaceutical Science*, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including Domb et al. 1992. *Polymers for Advanced Technologies* 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 g to about 100 mg, more preferably from about 1 µg to about 10 mg, even more preferably from about 10 µg to about 1 mg. The dose amount of an infectious RNA molecule of the present invention in a vaccine of the present invention preferably ranges from about 0.1 µg to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

In summary, our studies determined that individual N-linked glycosylation in glycoprotein E1 sites are not essential for viral particle formation or virus infectivity in cultured swine macrophages or the natural host, with one individual site, N594, involved in attenuation of the virulent parental virus. This study also showed that in the context of two or more putative glycosylation site modifications, residue N594 is critical for virus viability. The effective protective immunity elicited by E1.N3v and E1.N1N2v suggests that glycosylation of E1 could be modified for the development of live-attenuated vaccines. An improved understanding of the genetic basis of virus virulence and host range will permit future rational design of efficacious biological tools for controlling CSF.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al., supra) free of Bovine Viral Diarrhea Virus (BVDV) were cultured in Dulbecco's Minimal Essential Medium (DMEM, GIBCO, Grand Island, N.Y.) with 10% fetal calf serum (FCS, Atlas Biologicals, Fort Collins, Colo.). CSFV Brescia strain (obtained from the Animal and Plant Health Inspection Service, Plum Island Animal Disease Center) was propagated in SK6 cells and used for an infectious cDNA clone (Risatti et al. 2005a, supra). Growth kinetics were assessed on primary swine macrophage cell cultures prepared as described by Zsak et al. (1996. *J. Virol.* 70: 8865-8871). Titration of CSFV from clinical samples was performed using SK6 cells in 96-well plates (Costar, Cambridge, Mass.). Viral infectivity was detected, after 4 days in culture, by an immunoperoxidase assay using the CSFV monoclonal antibodies WH303 (Edwards et al. 1991. *Vet. Microbiol.* 29:101-108) and the Vectastain ABC kit (Vector Laboratories, Burlingame, Calif.). Titers were calculated using the method of Reed and Muench (1938. *American J. Hygiene* 27: 493-497) and expressed as $TCID_{50}$/ml. As performed, test sensitivity was $\geq 1.8$ TCID50/ml. Plaque assays were performed using SK6 cells in 6-well plates (Costar). SK6 monolayers were infected, overlaid with 0.5% agarose and incubated at 37° C. for 3 days. Plates were fixed with 50% (vol/vol) ethanol-acetone and stained by immunohistochemistry with mAb WH303.

Example 2

Construction of CSFV Glycosylation Mutants

A full-length infectious clone of the virulent Brescia isolate (pBIC) (Risatti et al. 2005a, supra) was used as a template in which N-linked glycosylation sites in the E1 glycoprotein were mutated. Glycosylation sites were predicted using analysis tools from the Center for Biological Sequence Analysis (Retrieved from the Internet: <URL: cbs.dtu.dk/services/). Mutations were introduced by site-directed mutagenesis using the QuickChange XL Site-Directed Mutagenesis kit (Stratagene, Cedar Creek, Tex.) performed per manufacturer's instructions and using the following primers (only forward primer sequences are shown); E1.N1v: TATGCCCTATCACCT TATTGT GCTSTGACAAGCAAAATAGGGTAC (SEQ ID NO:5); E1.N2v: GGGTACATAT GGTACACTAAC GCCTGTACCCCGGCTTGCCTCCCC (SEQ ID NO:6); E1.N3v: GAAG GCTGTGACACAAACCAGCTGGCTT-TAACAGTGGAACTCAGGACT(SEQ ID NO:7).

Example 3

In Vitro Rescue of CSFV Brescia and Glycosylation Mutants

Full-length genomic clones were linearized with SrfI and in vitro transcribed using the T7 Megascript system (Ambion, Austin, Tex.). RNA was precipitated with LiCl and transfected into SK6 cells by electroporation at 500 volts, 720 ohms, 100 watts with a BTX 630 electroporator (BTX, San Diego, Calif.). Cells were seeded in 12-well plates and incubated for 4 days at 37 EC and 5% $CO_2$. Virus was detected by immunoperoxidase staining as described above, and stocks of rescued viruses were stored at −70 EC.

Infectious RNA was in vitro transcribed from full-length infectious clones of the CSFV Brescia strain or a set of glycosylation mutants (Table 1, FIG. 1) and used to transfect SK6 cells. Mutants referred to as E1.N1, E1.N2, E1.N3 represent each of three putative glycosylation sites starting from the N terminus of E1 (Table 1), whereas multiple mutants are represented by combinations of indicated sites (FIG. 1A). Viruses were rescued from transfected cells by day 4 post-transfection. Nucleotide sequences of the rescued virus genomes were identical to parental DNA plasmids, confirming that only mutations at predicted glycosylation sites were reflected in rescued viruses.

TABLE 1

Set of CSFV E1 glycosylation mutant viruses constructed.

| E1 Position | Wild-Type Sequence | Mutant Sequence | Codon Change | Mutant |
|---|---|---|---|---|
| 500 | NVTS (SEQ ID NO: 8) | AVTS (SEQ ID NO: 9) | AAT→GCT | E1.N1 |
| 513 | NCTP (SEQ ID NO: 10) | ACTP (SEQ ID NO: 11) | AAC→GCC | E1.N2 |
| 594 | NLTV (SEQ ID NO: 12) | ALTV (SEQ ID NO: 13) | AAT→GCT | E1.N3 |
| 500/513 | NVTS/NCTP (SEQ ID NOs: 8/10) | AVTS/ACTP (SEQ ID NOs: 9/11) | AAT→GCT/ AAC→GCC | E1.N1N2 |
| 513/594 | NCTP/NLTV (SEQ ID NOs: 10/12) | ACTP/ALTV (SEQ ID NOs: 11/13) | AAC→GCC/ AAT→GCT | E1.N2N3 |
| 500/594 | NVTS/NLTV (SEQ ID NOs: 8/12) | AVTS/ALTV (SEQ ID NOs: 9/13) | AAT→GCT/ AAT→GCT | E1.N1N3 |
| 500/513/594 | NVTS/NCTP/NLTV (SEQ ID NOs: 8/10/12) | AVTS/ACTP/ALTV (SEQ ID NOs: 9/11/13) | AAT→GCT/ AAC→GCC/ AAT→GCT | E1.N1N2N3 |

Example 4

DNA Sequencing and Analysis

Full-length infectious clones and in vitro rescued viruses were completely sequenced with CSFV specific primers by the dideoxynucleotide chain-termination method (Sanger et al. 1977. *Proc. Natl. Acad. Sci. USA* 74: 5483-5487). Viruses recovered from infected animals were sequenced in the mutated area. Sequencing reactions were prepared with the Dye Terminator Cycle Sequencing Kit (Applied Biosystems, Foster City, Calif.). Reaction products were sequenced on a PRISM 3730xl automated DNA Sequencer (Applied Biosystems). Sequence data were assembled with the Phrap software program (http://www.phrap.org), with confirmatory assemblies performed using CAP3 (Huang et al. 1999.

Genome Res. 9: 868-877). The final DNA consensus sequence represented an average five-fold redundancy at each base position. Sequence comparisons were conducted using BioEdit software (Retrieved from the Internet: <URL: mbio.ncsu.edu/BioEdit/bioedit.html).

The DNA sequence encoding a modified CSFV E1 glycoprotein, i.e., E1.N1N2 is identified by SEQ ID NO: 1. The DNA sequence encoding a modified CSFV E1 glycoprotein, i.e., E1.N3 is identified by SEQ ID NO:3. The glycoproteins encoded by these DNA molecules are identified by SEQ ID NOs: 2 and 4, respectively.

Example 5

In Vitro and In Vivo Analysis of Glycosylation Mutants

In vitro growth characteristics of mutant viruses E1.N1v, E1.N2v, E.1N3v and E1.N1N2v were evaluated relative to parental BICv in a multistep growth curve (FIG. 1B). Primary porcine macrophage cell cultures were infected at a multiplicity of infection (MOI) of 0.1 $TCID_{50}$ per cell. Virus was adsorbed for 1 h (time zero), and samples were collected at times post-infection through 72 h.

All single glycosylation site mutants exhibited titers approximately an order lower than those corresponding to BICv. Additionally, when viruses were tested for their plaque size in SK6 cells, E1.N3v exhibited a noticeable reduction in plaque size relative to BICv (FIG. 1C). Interestingly, some viruses were not rescued from SK-6 cells transfected with RNA transcribed from full-length cDNA clones carrying multiple glycosylation site mutations (E1.N1N2N3, E1.N1N3 and E1.N2N3) that included substitutions at the E1.N3 position (N594).

To examine the effect of E1 glycosylation on CSFV virulence, and establish the impact of mutations at individual glycosylation sites in swine virulence, individual mutants were intranasally inoculated with $10^5$ $TCID_{50}$ and monitored for clinical disease relative to the parental virus. Swine used in all animal studies were 10 to 12 weeks old, forty-pound commercial bred pigs. For screening, 10 pigs were randomly allocated into 5 groups of 2 animals each, and pigs in each group were inoculated with one of the single glycosylation mutants, E1.N1N2v or BICv. Clinical signs (anorexia, depression, fever, purple skin discoloration, staggering gait, diarrhea and cough) and changes in body temperature were recorded daily throughout the experiment and scored as previously described (Mittelholzer et al. 2000. *Vet. Microbiol.* 74: 293-308).

BICv exhibited a characteristic virulent phenotype (Table 2). Animals infected with E1.N3v survived the infection and remained normal throughout the observation period (21 days). All animals infected with E1.N1v and E1.N2v presented clinical signs of CSF starting 5 to 8 DPI, with clinical presentation and severity similar to those observed in animals inoculated with BICv. White blood cell and platelet counts dropped by 4 to 6 DPI in animals inoculated with E1.N1 and E1.N2v, and BICv and kept declining until death, while a transient decrease was observed in animals inoculated with E1.N1v (FIG. 2). Since E1.N1v and E1.N2v were as virulent as the wild type BICv it was interesting to assess the influence on viral virulence of the simultaneous removal of both glycosylation sites. Two animals were infected with E1.N1N2v under the same conditions above described. Infected animals remained normal throughout the observation period (21 days) along with a transient decrease in the hematological (Table 2 and FIG. 2).

TABLE 2

Swine survival and fever response following infection with CSFV E1 glycosylation mutants and parental BICv.

| Virus | Survivor/ total | Mean time to death: Days ∀SD | Mean time of fever onset: Days ∀SD | Mean time of fever duration: Days ∀SD |
|---|---|---|---|---|
| BICv | 6/6* | 8.2 (0.9) | 3.4 (1.1) | 6.5 (0.9) |
| E1.N1v | 0/2 | 5.5 (0.7) | 2 (0.0) | 3.5 (0.7) |
| E1.N2v | 0/2 | 9.5 (2.1) | 3 (0.0) | 6.5 (2.1) |
| E1.N3v | 6/6* | — | — | — |
| E1.N1N2v | 6/6* | — | — | — |

*The original experiment performed with 2 animals was repeated with 4 more individuals. Presented results represent data from both experiments.

The capability of E1.N3v and E1.N1N2v to establish a systemic infection in intranasally inoculated animals was compared with that of virulent parental virus BICv. To assess the effect of the E1.N3v and E1.N1N2v mutation on virus shedding and distribution in different organs during infection, pigs were randomly allocated into 3 groups of 9 animals each and intranasally inoculated (see above) with E1.N3v, E1.N1N2v or BICv. One pig per group was sacrificed at 2, 4, 6, 8 and 12 DPI. Blood, nasal swabs and tonsil scraping samples were obtained from pigs at necropsy. Tissue samples (tonsil, mandibular lymph node, spleen and kidney) were snap-frozen in liquid nitrogen for subsequent virus titration. The remaining 4 pigs in each room were monitored to check for appearance of clinical signs during a 21-day period.

Virus shedding and viremia in E1.N3v and E1.N1N2v inoculated animals was undetectable while values in E1.N1v, E1.N2v were 1.5-2.5 logs below of those of BICv infected swine depending on the time post-infection (FIG. 2). In all cases partial nucleotide sequences of E2 protein from viruses recovered from infected animals were identical to those of stock viruses used for inoculation (data not shown).

Titers measured in tissue samples are shown in Table 3. In vivo replication of E1.N3v and E1.N1N2v were transient in tonsils with titers reduced up to $10^2$ to $10^5$, depending on the time post-infection, relative to those of BICv. Differences between E1.N3v and E1.N1N2v and BICv virus titers were also observed in mandibular lymph nodes, spleen, and kidney, indicating a limited capability of E1.N3v and E1.N1N2v to spread within the host.

TABLE 3

Titers of virus in tissues after intranasal inoculation with mutant E1.N1N2v, E1.N3v or parental BICv.

| | | $Log_{10}TCID_{50}/g$ in: | | | |
|---|---|---|---|---|---|
| Virus | DPI | Tonsil | Mandibular Lymph Node | Spleen | Kidney |
| E1.N1N2v | 2 | n.d.* | 2.63 | 1.97 | n.d. |
| | 4 | 4.47 | n.d. | n.d. | 1.97 |
| | 6 | 3.63 | n.d. | 2.13 | 2.47 |
| | 8 | 2.8 | n.d. | n.d. | n.d. |
| | 12 | n.d. | n.d. | n.d. | n.d. |
| E1.N3v | 2 | 2.3 | n.d. | 2.13 | 2.8 |
| | 4 | 1.97 | n.d. | 1.97 | n.d. |
| | 6 | 2.3 | n.d. | 2.47 | 2.47 |
| | 8 | 7.8 | n.d. | 1.97 | n.d. |
| | 12 | n.d. | n.d. | 1.97 | 2.13 |
| BICv | 2 | 3.12 | 1.97 | n.d. | n.d. |
| | 4 | 7.13 | 3.8 | 2.97 | 2.8 |
| | 6 | 6.8 | 6.13 | 6.13 | 5.13 |
| | 8 | 7.13 | 4.97 | 7.13 | 5.47 |
| | 12 | D# | D | D | D |

*n.d. (not detectable): virus titers equal or less than 1.8 $TCID_{50}$ ($log_{10}$).
D, animals in this group were all dead by this time point.

Example 6

Immunization, Challenge, and Clinical Analysis

For protection studies, 18 pigs were randomly allocated into 5 groups of 4 animals each. Pigs in groups 1 and 2 were inoculated with E1.N1N2v, pigs in groups 3 and 4 were inoculated with E1.N3v and pigs in group 5 were mock infected. At 3 DPI (groups 1 and 3) or 28 DPI (groups 2 and 4), animals were challenged with BICv along with animals in group 5. Clinical signs and body temperature were recorded daily throughout the experiment as described above. Blood, serum, nasal swabs and tonsil scrapings were collected at times post-challenge, with blood obtained from the anterior vena cava in EDTA-containing tubes (Vacutainer) for total and differential white blood cell counts. Total and differential white blood cell and platelet counts were obtained using a Beckman Coulter ACT (Beckman, Coulter, Calif.).

The limited in vivo replication kinetics of E1.N3v and E1.N1N2v is similar to that observed with CSICv (Risatti et al. 2005a, supra), a CSFV vaccine strain. However, restricted viral in vivo replication could also impair protection against wild-type virus infection. Thus, the ability of E1.N3v and E1.N1N2v to induce protection against virulent BICv was assessed in early and late vaccination-exposure experiments.

Mock-vaccinated control pig groups receiving BICv only (n=2) developed anorexia, depression, and fever by 4 days post-challenge (DPC), and a marked reduction of circulating leukocytes and platelets by 4 DPC (data not shown), and died or were euthanized in extremis by 9 DPC (Table 4). Notably, E1.N3v and E1.N1N2v induced complete protection by 3 DPI. All pigs survived infection and remained clinically normal, without significant changes in their hematological values (data not shown). Pigs challenged at 28 days post N1v infection were also protected, remaining clinically normal, without alterations of hematological profiles (data not shown).

TABLE 4

Detection of virus in nasal swabs, tonsil scrapings, and blood samples obtained after challenge of E1.N1N2v- or E1.N3v-vaccinated animals with virulent BICv.

| Challenge Group | Sample | Days Post-Challenge | | | | | | |
|---|---|---|---|---|---|---|---|---|
| | | 0 | 4 | 6 | 8 | 12 | 14 | 21 |
| E1.N1N2v 3DPI | Nasal | 0/4* | 1/4 (1.9) | 1/4 (2.5) | 1/4 (3.1) | 0/4 | 0/4 | 0/4 |
| | Tonsil | 0/4 | 1/2 (2.1) | 1/4 (2.8) | 2/4 (2.7) | 0/4 | 0/4 | 0/4 |
| | Blood | 0/4 | 1/2 (2.9)# | 3/4 (4) | 1/4 (4.8) | 0/4 | 0/4 | 0/4 |
| E1.N1N2v 28DPI | Nasal | 0/4 | 0/4 | 0/4 | 0/4 | 0/4 | 0/4 | 0/4 |
| | Tonsil | 0/4 | 0/4 | 0/4 | 0/4 | 0/4 | 0/4 | 0/4 |
| | Blood | 0/4 | 0/4 | 0/4 | 0/4 | 0/4 | 0/4 | 0/4 |
| E1.N3v 3DPI | Nasal | 0/4 | 0/4 | 0/4 | 0/4 | 0/4 | 0/4 | 0/4 |
| | Tonsil | 0/4 | 0/4 | 0/4 | 0/4 | 0/4 | 0/4 | 0/4 |
| | Blood | 0/4 | 0/4 | 0/4 | 0/4 | 0/4 | 0/4 | 0/4 |
| E1.N3v 28DPI | Nasal | 0/4* | 0/4 | 0/4 | 0/4 | 0/4 | 0/4 | 0/4 |
| | Tonsil | 0/4 | 0/4 | 0/4 | 0/4 | 0/4 | 0/4 | 0/4 |
| | Blood | 0/4 | 0/4 | 0/4 | 0/4 | 0/4 | 0/4 | 0/4 |
| Control 3DPI | Nasal | 0/2 | 0/2 | 2/2 (2.1) | 2/2 (5.1) | D | | |
| | Tonsil | 0/2 | 1/2 (2.1) | 2/2 (2.7) | 2/2 (4.1) | | | |
| | Blood | 0/2 | 1/2 (2.2) | 2/2 (6.4) | 2/2 (7.2) | | | |
| Control 28DPI | Nasal | 0/2 | 0/2 | 1/2 (2.1) | 2/2 (3.6) | D | | |
| | Tonsil | 0/2 | 1/2 (1.9) | 2/2 (4.2) | 2/2 (3.6) | | | |
| | Blood | 0/2 | 1/2 (2.1) | 2/2 (5.1) | 2/2 (7.1) | | | |

*Number of animals positive for isolated virus over total number of challenged animals.
Number in parentheses indicates average virus titers expressed as $\log_{10} TCID_{50}$/ml for four animals.
D Animals in this group were all dead by this time point.

Viremia and virus shedding of vaccinated-exposed animals was examined at 4, 6, 8, 14 and 21 DPC (Table 4). As expected, in mock-vaccinated control animals, viremia was observed by 4 DPC, with virus titers remaining high by 8 DPC (approximately $10^7$ $TCID_{50}$/ml). Furthermore, virus was detected in nasal swabs and tonsil scrapings of these animals after 4 DPC. Conversely, viremia was detected by 4 DPC in all clinical samples of one of the four E1.N1N2v-infected animals challenged at 3 DPI, while no virus was detected in any sample from E1.N3v-infected animals at any time post challenge (Table 4). Virus was not detected in clinical samples obtained from any E1.N3v- or E1.N1N2v-infected pigs challenged at 28 DPI. Therefore, even though E1.N3v and E1.N1N2v showed a limited in vivo growth, a solid protection was induced shortly after vaccination.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated polynucleotide molecule comprising a DNA sequence encoding an infectious RNA molecule that encodes a genetically modified classical swine fever virus (CSFV) mutant of the highly pathogenic native Brescia strain, wherein said CSFV mutant encodes a genetically modified E1 glycoprotein set forth in SEQ ID NO:3, wherein mutated non-glycosylated amino acid alanine in the sequence AVTS (SEQ ID NO:9) has replaced glycosylated asparagine in the sequence NVTS (SEQ ID NO:8) at position 500 and mutated non-glycosylated amino acid alanine in the sequence ACTP (SEQ ID NO:11) has replaced glycosylated asparagine in the sequence NCTP (SEQ ID NO:10) at position 513, said mutated amino acids having a glycosylation pattern different from the amino acids present in positions 500 and 513 of said highly pathogenic native Brescia strain, wherein said genetically modified CSFV mutant is attenuated and unable to produce a pathogenic CSFV infection in a porcine animal.

2. The isolated polynucleotide molecule of claim 1, wherein said DNA sequence is SEQ ID NO: 1 or its complement thereof.

3. A genetically modified CSFV mutant, wherein the CSF virus is encoded by the isolated polynucleotide molecule of claim 1.

4. A CSF vaccine comprising a genetically modified CSFV mutant that does not produce CSF disease in swine, wherein said virus is encoded by the polynucleotide of claim 1.

5. An isolated recombinant classical swine fever virus comprising the RNA molecule according to claim 1, said RNA molecule encodes a genetically modified CSFV E1 glycoprotein having the sequence identified by SEQ ID NO:3.

6. A vaccine for protecting a porcine animal against infection by a CSFV, which vaccine comprises (a) a genetically modified CSFV encoded by an infectious RNA molecule encoded by the polynucleotide molecule according to claim 1, (b) said infectious RNA molecule of claim 1, wherein the vaccine is in an effective amount to produce immunoprotection against a CSFV infection; and a carrier acceptable for veterinary use.

7. A recombinant classical swine fever virus comprising DNA encoding a mutated CSFV E1 glycoprotein having the sequence identified by SEQ ID NO: 3, a modification resulting in attenuation of CSFV.

8. A plasmid capable of directly transfecting a suitable host cell and expressing a genetically modified CSFV from the suitable host cell so transfected, which plasmid comprises a) the DNA sequence of claim 1, and b) a promoter capable of transcribing said infectious RNA molecule in said suitable host cell.

9. A host cell transfected with the polynucleotide molecule of claim 1.

10. A rationally designed live attenuated CSF vaccine comprising a recombinant classical swine fever virus according to claim 6.

11. A method of immunizing an animal against CSF, comprising administering to said animal, a vaccine comprising a recombinant classical swine fever virus according to claim 6.

12. A method of protecting an animal against CSF, comprising administering to said animal an effective amount of the vaccine of claim 6 to protect said animal from clinical CSF.

13. A method of producing an attenuated recombinant classical swine fever virus comprising DNA encoding a modified CSFV E1 glycoprotein, comprising:
   (a) mutating a region of the E1 gene of the highly pathogenic strain Brescia, wherein said region encodes the modified CSFV E1 glycoprotein set forth in SEQ ID NO:3, and whereby mutations in said DNA result in a change in the glycosylation pattern characteristic of CSFV E1 glycoprotein; and
   (b) achieving attenuation of CSFV as a result of such modification.

* * * * *

SEQUENCE LISTING

<160> NUMBER OF SEQ ID NOS: 13

<210> SEQ ID NO 1
<211> LENGTH: 12297
<212> TYPE: DNA
<213> ORGANISM: Classical Swine Fever Virus

<400> SEQUENCE: 1

```
gtatacgagg ttagttcatt ctcgtgtaca tgattggaca aatcaaaatc tcaatttggt      60
tcagggcctc cctccagcga cggccgagct gggctagcca tgcccacagt aggactagca     120
aacggaggga ctagccgtag tggcgagctc cctgggtggt ctaagtcctg agtacaggac     180
agtcgtcagt agttcgacgt gagcagaagc ccacctcgag atgctatgtg gacgagggca     240
tgcccaagac acaccttaac cctagcgggg gtcgttaggg tgaaatcaca ccatgtgatg     300
ggagtacgac ctgatagggt gctgcagagg cccactatta ggctagtata aaaatctctg     360
ctgtacatgg cacatggagt tgaatcattt tgaactttta tacaaaacaa acaaacaaaa     420
accaatggga gtggaggaac cggtatacga tgtaacgggg agaccattgt ttggagaccc     480
aagtgaggta cacccacaat caacattgaa gctaccacat gataggggga gaggcaacat     540
caaaacaaca ctgaagaacc tacctaggag aggtgactgc aggagtggca accacctagg     600
cccggttagt gggatatatg taaagcccgg ccctgtcttt tatcaggact acatgggccc     660
agtctatcat agagccctc tagagttttt tgacgaagca cagttttgtg aggtgaccaa     720
aaggataggt agggtgacag gtagtgacgg aaagctttac catatatacg tgtgcatcga     780
tggttgcatc ctgctgaagc tagccaagag gggcgagcca agaaccctga agtggattag     840
aaatctcacc gactgtccat tgtgggttac cagttgttct gatgatggtg caagtgcaag     900
taaagagaag aaaccagata ggatcaacaa gggtaaatta agatagccc caaagagca     960 tgagaaggac agcaggacta agccacctga tgctacgatt gtagtggaag gagtaaaata    1020
ccaggtcaaa aagaaaggta aagttaaggg aaagaatacc caagacggcc tgtaccacaa    1080
caagaataaa ccaccagaat ctaggaagaa attagaaaaa gccctattgg catgggcagt    1140
gatagcaatt atgttatacc aacctgttgc agccgaaaat ataactcaat ggaacctgag    1200
tgacaacggt accaatggta tccagcacgc tatgtacctt agaggagtca gcagaagctt    1260
gcatgggatc tggccagaaa aaatatgcaa aggagtcccc acctacctgg ccacagacac    1320
ggaactgaga gaaatacagg gaatgatgga tgccagcgag gggacaaact atacgtgctg    1380
taagttacag agacatgaat ggaacaaaca tggatggtgt aactggtata acatagaccc    1440
ctggatacag ttgatgaata gaacccaagc aaacttggca gaaggccctc cgagcaagga    1500
gtgcgccgtg acttgcaggt acgataaaaa tgctgacatt aacgtggtca cccaggccag    1560
aaacaggcca accaccctaa ctggctgcaa gaaagggaaa aattttttctt ttgcgggtac    1620 agttatagag ggcccatgta atttcaacgt ttctgttgag gatatcttat atggggatca    1680
tgagtgtggc agtctactcc aggatacggc tctataccta gtagatggaa tgaccaacac    1740
tatagagaga gccaggcagg gagccgcgag ggtgacatct tggctaggga ggcaactcag    1800
aactgccggg aagaggttgg agggcagaag caaaacctgg tttggtgcct atgccctatc    1860
accttattgt gctgtgacaa gcaaaatagg gtacatatgg tacactaacg cctgtacccc    1920
ggcttgcctc cccaaaaata caaagataat aggccccggt aaatttgaca ctaacgcgga    1980
agacggaaag attctccatg agatgggggg ccacctatca gaatttctgc tgctctctct    2040
ggtcgttctg tctgacttcg cccctgaaac agccagcgcg ttatacctca ttttgcacta    2100
cgtgatccct caatcccatg aagaacctga aggctgtgac acaaaccagc tgaatttaac    2160
agtggaactc aggactgaag acgtgatacc atcatcagtc tggaatgttg caaatatgt    2220 gtgtgttaga ccagactggt ggccatatga aaccaaggtg ctttgttat ttgaagaggc    2280 aggacaggtc gtaaagttag ccttgcgggc actgagggat ttaaccaggg tctggaatag    2340
cgcatcaacc acggcattcc tcatctgctt gataaaagta ttaagaggac aggtcgtgca    2400
```

-continued

```
aggtgtgata tggctgttac tggtaactgg ggcacaaggc cggctagcct gcaaggaaga    2460
tcacaggtac gctatatcaa caaccaatga gatagggcta cttggggccg aaggtctcac    2520
taccacctgg aaagaataca accacaattt gcaactggat gatgggaccg tcaaggccat    2580
ctgcatggca ggttcctttta aagtcacagc acttaatgtg gttagtagga ggtatctggc   2640
atcattacat aaggacgctt tacccacttc cgtgacattc gagctcctgt tcgacgggac    2700
cagcccattg accgaggaaa tgggagatga cttcgggttc ggactgtgtc cgtatgatac    2760
gagccctgta gtcaagggaa agtacaacac aaccttgttg aatggtagtg cattctacct    2820
agtttgccca ataggggtgga cgggtgttat agagtgcacg gcagtgagcc cgacaactct   2880
gagaacagaa gtggtaaaga ccttcagaag agagaaaccc tttccgtaca gaagggattg    2940
tgtgaccact acagtggaaa atgaagatct attctactgt aaatgggggg gcaattggac    3000
atgtgtgaaa ggtgaaccag tgacctacac gggggggcca gtaaaacaat gcagatggtg    3060
tggcttcgac ttcaatgagc ctgacggact cccacactac cccataggta agtgcatttt    3120
ggcaaatgag acaggttaca gaatagtgga ttcaacggac tgtaacagag atggcgttgt    3180
aatcagcaca gaggggagtc atgagtgctt gattggtaac acaactgtca aggtgcatgc    3240
attagatgaa agactaggcc ctatgccatg caggcctaag gagatcgtct ctagtgcggg    3300
acctgtaagg aaaacttcct gtacattcaa ctacgcaaaa actctgagga acaggtatta    3360
tgagcccagg gacagctatt tccaacaata tatgctcaag ggcgagtatc agtactggtt    3420
tgatctggat gtgaccgacc gccactcaga ttacttcgca gaattcattg tcttggtggt    3480
ggtggcactg ttgggaggaa gatatgtcct gtggctaata gtgacctaca tagttctaac    3540
agaacaactc gccgctggtc tacagttagg ccagggtgag gtagtgttaa tagggaactt    3600
aatcacccac acagatattg aggttgtagt atatttctta ctgctctatt tggtcatgag    3660
agatgagcct ataaagaaat ggatactact gctgttccat gctatgacca acaatccagt    3720
taagaccata acagtggcac tgctcatggt tagcgggggtt gccaagggtg aaagatagat   3780 tggtggtttgg cagcggctgc cggagaccaa ctttgatatc caactcgcgc tgacagttat   3840
agtagtcgct gtgatgttgc tggcaaagaa agatccgact accgtcccct tggttataac    3900
ggtggcaacc ctgagaacgg ctaagataac taatggactt agtacagatc tagccatagc    3960
tacagtgtca acagctttgc taacctggac ctacattagt gactattata aatacaagac    4020
cttgctacag taccttatta gcacagtgac aggtatcttc ttgataaggg tactgaaggg    4080
ggtaggtgag ttagatttac acaccccaac cttaccatct tacagacccc tcttcttcat    4140
cctcgtgtac ctcatttcca ctgcagtggt aacaagatgg aatctggaca tagccggatt    4200
gctgctgcag tgtgtcccaa ccctttttaat ggttttcacg atgtgggcag acatccttac   4260
cctgatcctc atactgccta cttacgagtt gacaaaacta tattacctca aggaagtgaa    4320
gattggggca gaaagggggct ggttgtggaa gaccaacttc aagagggtaa atgacatata   4380
cgaagttgac caagctggtg aggggggtgta ccttttccca tcaaaacaaa agacaggtac   4440
aataacaggt actatgttgc cattgatcaa agccatactc ataagttgca tcagcaataa    4500
gtggcaattt atatatctat tgtacttgat attcgaagtg tcttactacc ttcacaagaa    4560
gatcatagat gaaatagcag gagggaccaa cttcatctcg agacttgtag ccgctctgat    4620
tgaagccaat tgggccttttg acaacgaaga agttagaggt ttaaagaagt tcttcctgct   4680
gtctagtagg gttaaagaac tgatcatcaa acacaaagtg aggaatgaag tgatggtcca    4740
ctggtttggc gacgaagagg tctatgggat gccgaagctg gttggcttag tcaaggcagc    4800
```

```
aacactgagt aaaaataaac attgtatttt gtgcaccgtc tgtgaaaaca gagagtggag    4860
aggagaaacc tgcccaaaat gcggccgttt tgggccacca gtgacctgtg gcatgaccct    4920
agccgacttt gaagaaaaac actataagag gattttcttt agagaggatc aatcagaagg    4980
gccggttagg gaggagtatg cagggtatct gcaatataga gccagagggc aattattcct    5040
gaggaatctc ccggtgctag caacaaaagt caagatgctc ctggtcggaa atcttgggac    5100
ggaggtgggg gatttggaac accttggctg ggtgctcaga gggcctgccg tttgcaagaa    5160
ggttaccgaa catgagaaat gcaccacatc cataatggac aaattaactg ctttcttcgg    5220
tgttatgcca aggggcacca cacctagagc ccctgtgaga ttccccacct ctctcttaaa    5280
gataagaagg gggctggaaa ctggctgggc gtacacacac caaggtggca tcagttcagt    5340
ggaccatgtc acttgtggga aagacttact ggtatgtgac actatgggcc ggacaagggt    5400
tgtttgccaa tcaaataaca agatgacaga cgagtccgag tatggagtta aaactgactc    5460
cggatgcccg gagggagcta ggtgttacgt gttcaaccca gaggcagtta acatatccgg    5520
gactaaagga gccatggtcc acttacaaaa aactggagga gaattcaccc tgtgtgacagc   5580
atcagggact ccgccttcct tgatctcaa gaacctcaaa ggctggtcag ggctgccgat     5640
atttgaggca tcaagtggaa gagtagtcgg cagggttaag gtcgggaaga atgaggactc    5700
taaaccaacc aagcttatga gtggaataca acagtctcc aaaagtacca cagacttgac     5760
agaaatggta aagaaaataa caaccatgaa caggggagaa ttcagacaaa taaccccttgc   5820
cacaggtgcc ggaaaaacca cggaactccc tagatcagtc atagaagaga taggaaggca    5880
taagagggtc ttggtcttga tccctctgag ggcggcagca gagtcagtat accaatatat    5940
gagacaaaaa cacccaagca tagcattcaa cttgaggata ggggagatga aggaagggga    6000
catggccaca gggataacct atgcctcata tggttacttc tgtcagatgc acaacctaa     6060
gctgcgagcc gcgatggttg agtactcctt catattcctt gatgagtacc actgtgccac    6120
ccccgaacaa ttggctatca tgggaaagat ccacagattt tcagagaacc tgcgggtagt    6180
agccatgacc gcaacaccag caggcacggt aacaactaca gggcaaaaac accctataga    6240
agaatacata gccccagaag tgatgaaggg ggaagactta ggttcagagt acttggacat    6300
agctggacta aagataccag tagaggagat gaagagtaac atgctggtct ttgtgcccac    6360
aaggaacatg gctgtagaga cggcaaagaa actgaaagct aagggttata actcaggcta    6420
ctattatagt ggagaggatc catctaacct gagggtggta acatcacagt ccccgtacgt    6480
ggtggtagca accaacgcaa tagaatcagg tgttactctc ccagacttgg atgtggtcgt    6540
cgacacaggg cttaagtgtg aaaagaggat acggctgtca cctaagatgc ccttcatagt    6600
gacgggcctg aagagaatgg ctgtcacgat tgggaacaa gcccagagaa ggggagagt     6660
tgggagagtg aagcctggga gatactacag gagtcaagaa accccgttg gttccaaaga    6720
ttaccattac gacctactgc aagcacagag gtacggtata aagatgggga taaacatcac    6780
caaatctttt agagagatga attatgattg gagcctttat gaggaggata gtctgatgat    6840
tacacaattg gaaatcctca caatctgtt gatatcagaa gagctaccaa tggcagtaaa     6900
aaatataatg gccaggactg accacccaga accaatccaa ctggcgtaca acagctacga    6960
aacgcaggtg ccagtgctat tcccaaaaat aaaaaatgga gaggtgactg acagttacga    7020
taactatacc ttcctcaacg caagaaagct gggggatgat gtacctccct acgtgtatgc    7080
cacagaggat gaggacttag cggtagagct gctgggctta gactggccgg accctgggaa    7140
ccaaggaacc gtggaggctg gtagagcact aaaacaagta gttggtctat caacagctga    7200
```

```
gaacgccctg ttagtagctt tattcggcta tgtaggatat caggcactct caaagaggca    7260
tataccagta gtcacagaca tatattcaat tgaagatcac aggttggaag acaccacaca    7320
cctacagtat gccccgaatg ctatcaagac ggaggggaag gagacagaat tgaaggagct    7380
agctcagggg gatgtgcaga gatgtatgga agctatgact aattatgcaa gagatggcat    7440
ccaattcatg aagtctcagg cactgaaagt gaaagaaacc cccacttaca aagagacaat    7500
ggacaccgtg gcggactatg taaagaagtt catggaggca ctggcggaca gcaaagaaga    7560
catcataaaa tatgggttgt gggggacgca cacaacctta tataagagca tcggtgctag    7620
gcttgggaac gagactgcgt tcgctaccct ggtcgtgaaa tggctggcat ttgggggaga    7680
atcaatagca gaccatgtca aacaagcggc cacagacttg gtcgtttact atatcatcaa    7740
cagacctcag ttcccaggag acacggagac acaacaggaa ggaaggaaat ttgtagccag    7800
cctactggtc tcagccctgg ctacttacac ttacaaaagc tggaattaca ataatctgtc    7860
caagatagtt gaaccggctt tggctactct gccctatgcc gccacagctc tcaagctatt    7920 cgccccact cgattggaga gcgttgtcat actgagtacc gcaatctaca aaacctacct    7980
atcaatcagg cgcggaaaaa gcgatggttt gctaggcaca ggggttagtg cggctatgga    8040
aatcatgtca caaaacccag tatctgtggg tatagcggtc atgctagggg tgggggccgt    8100
agcggcccac aatgcaatcg aagccagtga gcagaagaga acactactca tgaaagtttt    8160
tgtaaagaac ttcttggatc aggcagccac tgatgaatta gtcaaggaga gccctgagaa    8220
aataataatg gctttgtttg aagcagtgca gacagtcggc aaccctctta gactggtata    8280
ccacctttac ggagtttttt acaaagggtg ggaggcaaaa gagttggccc aaaggacagc    8340
cggtaggaat ctttttcactt tgataatgtt tgaggctgtg gaactactgg gagtagatag    8400
cgaaggaaag atccgccagc tatcaagcaa ttacatacta gagctcctgt ataagttccg    8460
tgacagtatc aagtccagcg tgaggcagat ggcaatcagc tgggcccctg cccctttag    8520 ttgtgattgg acaccgacgg atgacagaat agggcttccc caagataatt tcctccgagt    8580
ggagacaaaa tgcccctgtg gttacaagat gaaagcagtt aagaattgtg ctggggagtt    8640
gagactctta gaagaggaag gctcatttct ctgcaggaat aaattcggga gaggttcacg    8700 gaactcagg gtgacaaaat actatgatga caatctatca gaaataaagc cagtgataag    8760
aatggaagga catgtggaac tctactacaa gggagccact attaaactgg atttcaacaa    8820
cagtaaaaca atattggcaa ccgataaatg ggaggtcgat cactccactc tggtcagggt    8880
gctcaagagg cacacagggg ctggatatcg tggggcatac ctgggtgaga aaccgaacca    8940
caaacatctg atagagaggg actgcgcaac catcaccaaa gataaggttt gtttttctcaa    9000 gatgaagaga gggtgtgcat ttacttatga cttatcccct cacaacctta cccggctgat    9060
cgaattggta cacaagaata acttggaaga caaagagatt cctgccgtta cggtcacaac    9120
ctggctggct tacacatttg taaatgaaga tatgggacc ataaaaccag ccttcggga    9180 gaaaataaca ccagagatgc aggaggagat aaccttgcag cctgctgtag tggtggatgc    9240
aactgacgtg accgtgaccg tggtagggga aacccctact atgactacag gggagacccc    9300
aacaacgttc accagctcag gtccagaccc gaaaggccaa caagttttaa aactgggagt    9360
aggtgaaggc caataccccg ggactaatcc acagagagca agcctgcacg aagccataca    9420
aagcgcagat gaaaggccct ctgtgttgat attggggtct gataaagcca cctctaatag    9480
agtgaaaact gtaaagaatg tgaaggtata cagaggcagg gacccactag aagtgagaga    9540
tatgatgagg aggggaaaga tcctagtcat agccctgtct agggttgata atgctctatt    9600
```

```
gaaatttgta gattacaaag gcacctttct aactagagag accctggagg cattaagttt      9660
gggtaggcca aaaagaaaaa acataaccaa ggcagaagca cagtggttgc tgcgcctcga      9720
agaccaaatg gaagagctac ccgattggtt cgcagccggg aacccatttt ttttagaggc      9780
caatattaaa catgacaggt atcatctggt aggggatata gctactatca aagagaaagc      9840
caaacaattg ggggctacag actctacaaa gatatccaag gaggttggtg caaaagtata      9900
ttctatgaaa ttgagtaatt gggtgatgca agaagaaaac aaacagagca acttgacccc      9960
cttatttgaa gagctcctac agcagtgtcc acccggaggc caaaacaaaa ctgcacatat     10020
ggtctctgct taccaactag ctcaagggaa ctggatgcca accagctgcc atgtttttat     10080
ggggaccata tctgccagaa ggactaagac ccatccatat gaagcatatg tcaagttaag     10140
ggagttggta gaggaacaca agatgaaaac attgtgtccc ggatcaagtc tgcgtaagca     10200
caatgaatgg gtaattggca agatcaaata ccagggcaac ctgaggacca aacacatgtt     10260
gaacccccggc aagtggcag agcaactgca cagagaagga cacagacaca atgtgtataa     10320
caagacaata ggctcagtga tgacagctac tggcatcagg ttggagaagt tgcccgtggt     10380
tagggcccag acagacacaa ccaacttcca ccaagcaata agggataaga tagacaagga     10440
agagaatcta cagaccccgg gtttacataa gaaactaatg gaagttttca atgcattgaa     10500
acgacccgag ttagagtcct cctatgacgc tgtggaatgg gaggaattgg agagaggaat     10560
aaacagaaag ggtgctgctg gtttctttga acgcaaaaac atagggagaa tattggattc     10620
agagaaaaat aaagtagaag agattattga caatctgaaa aagggtagaa atatcaaata     10680
ctatgaaacc gcaatcccaa aaaatgaaaa gagggatgtc aatgatgact ggaccgcagg     10740
tgactttgtg gacgagaaga aacccagagt catacaatac cctgaagcaa aaacaaggct     10800
ggccatcacc aaggtgatgt ataagtgggt gaagcagaag ccagtagtca tacccgggta     10860
tgaagggaag acacctctgt tccaaatttt tgacaaagta agaaggaat gggatcaatt     10920
ccaaaatcca gtggcagtga gcttcgacac taaggcgtgg acacccagg tgaccacaaa     10980
tgatctggag ctgataaagg acatacaaaa gtactacttc aagaagaaat ggcataaatt     11040
tattgacacc ctgactatgc atatgtcaga agtacccgta atcactgctg atggggaggt     11100
gtatataagg aaagggcaaa gaggtagtgg acagcccgac acaagcgcag gcaacagcat     11160
gctaaatgtg ttaacaatgg tttatgcctt ctgcgaggcc acaggggtac cctacaagag     11220
ttttgacagg gtggcaaaaa ttcatgtgtg cggggacgat ggtttcctga tcacagagag     11280
agctctcggc gagaaattcg caagcaaggg agtccaaatc ctgtatgaag ctgggaagcc     11340
ccagaagatc actgaagggg acaaaatgaa agtggcctac caatttgatg atattgagtt     11400
ttgctcccat acaccaatac aagtaaggtg gtcagataac acttctagct acatgccagg     11460
gagaaataca accacaatcc tggctaaaat ggccacaagg ttagattcca gtggtgagag     11520
gggtaccata gcgtacgaga aagcagtagc attcagcttc ctgctaatgt attcctggaa     11580
cccactaatc agaaggattt gcttattggt actatcaact gaactgcaag tgaaaccagg     11640
gaagtcaacc acttactatt atgaagggga cccgatatct gcctacaagg aagtcatcgg     11700
ccacaatctt ttcgatctca agagaacaag cttcgagaag ctggccaagt taaatctcag     11760
catgtccgta ctcgggggcct ggactagaca caccagcaaa agactactac aagactgtgt     11820
caatatgggt gttaaagagg caactggttc agtcaatgca gacagactgg tgagtagtaa     11880
gactggaaat aggtatgtac ctggagaagg ccacaccctg caaggagac attatgaaga     11940
actggtgttg gcaagaaaac agatcaacag cttccaaggg acagacaggt acaatctagg     12000
```

```
cccaatagtc aacatggtgt taaggaggct gagagtcatg atgatgaccc tgataggggag   12060 aggggtatga gtgcgggtga cccgcgatct ggacccgtca gtaggaccct attgtagata   12120
acactaattt tttatttatt tagatattac tatttattta tttatttatt tattgaatga   12180
gtaagaactg gtacaaacta cctcatgtta ccacactaca ctcattttaa cagcactta   12240 gctggaagga aaattcctga cgtccacagt tggactaagg taatttccta acggccc      12297
```

<210> SEQ ID NO 2
<211> LENGTH: 12297
<212> TYPE: DNA
<213> ORGANISM: Classical Swine Fever Virus
<400> SEQUENCE: 2

```
gtatacgagg ttagttcatt ctcgtgtaca tgattggaca aatcaaaatc tcaatttggt     60
tcagggcctc cctccagcga cggccgagct gggctagcca tgcccacagt aggactagca   120 aacgaggga ctagccgtag tggcgagctc cctgggtggt ctaagtcctg agtacaggac    180
agtcgtcagt agttcgacgt gagcagaagc ccacctcgag atgctatgtg gacgagggca   240
tgcccaagac acaccttaac cctagcgggg gtcgttaggg tgaaatcaca ccatgtgatg   300
ggagtacgac ctgatagggt gctgcagagg cccactatta ggctagtata aaatctctg   360 ctgtacatgg cacatggagt tgaatcattt tgaactttta tacaaaacaa acaaacaaaa   420
accaatggga gtggaggaac cggtatacga tgtaacgggg agaccattgt ttggagaccc   480
aagtgaggta cacccacaat caacattgaa gctaccacat gatagggga gaggcaacat    540 caaaacaaca ctgaagaacc tacctaggag aggtgactgc aggagtggca accacctagg   600
cccggttagt gggatatatg taaagcccgg ccctgtcttt tatcaggact acatgggccc   660
agtctatcat agagcccctc tagagttttt tgacgaagca cagttttgtg aggtgaccaa   720
aaggataggg agggtgacag gtagtgacgg aaagctttac catatatacg tgtgcatcga   780
tggttgcatc ctgctgaagc tagccaagag gggcgagcca agaaccctga agtggattag    840
aaatctcacc gactgtccat tgtgggttac cagttgttct gatgatggtg caagtgcaag    900
taaagagaag aaaccagata ggatcaacaa gggtaaatta agatagccc caaaagagca    960 tgagaaggac agcaggacta agccacctga tgctacgatt gtagtggaag gagtaaaata   1020
ccaggtcaaa agaaaggta agttaaggg aaagaatacc caagacggcc tgtaccacaa    1080
caagaataaa ccaccagaat ctaggaagaa attagaaaaa gccctattgg catgggcagt    1140
gatagcaatt atgttatacc aacctgttgc agccgaaaat ataactcaat ggaacctgag    1200
tgacaacggt accaatggta tccagcacgc tatgtacctt agaggagtca gcagaagctt    1260
gcatgggatc tggccagaaa aaatatgcaa aggagtcccc acctacctgg ccacagacac    1320
ggaactgaga gaaatacagg gaatgatgga tgccagcgag gggacaaact atacgtgctg    1380
taagttacag agacatgaat ggaacaaaca tggatggtgt aactggtata acatagaccc   1440
ctggatacag ttgatgaata gaacccaagc aaacttggca gaaggccctc cgagcaagga    1500
gtgcgccgtg acttgcaggt acgataaaaa tgctgacatt aacgtggtca cccaggccag    1560
aaacaggcca accacctaa ctggctgcaa gaaagggaaa aatttttctt ttgcgggtac     1620
agttatagag ggcccatgta atttcaacgt ttctgttgag gatatcttat atgggggatca   1680 tgagtgtggc agtctactcc aggatacggc tctataccta gtagatggaa tgaccaacac    1740
tatagagaga gccaggcagg gagccgcgag ggtgacatct tggctaggga ggcaactcag    1800
aactgccggg aagaggttgg agggcagaag caaaacctgg tttggtgcct atgccctatc    1860
```

```
accttattgt aatgtgacaa gcaaaatagg gtacatatgg tacactaaca actgtacccc    1920
ggcttgcctc cccaaaaata caaagataat aggccccggt aaatttgaca ctaacgcgga    1980
agacggaaag attctccatg agatgggggg ccacctatca gaatttctgc tgctctctct    2040
ggtcgttctg tctgacttcg cccctgaaac agccagcgcg ttatacctca ttttgcacta    2100
cgtgatccct caatcccatg aagaacctga aggctgtgac acaaaccagc tggctttaac    2160
agtggaactc aggactgaag acgtgatacc atcatcagtc tggaatgttg gcaaatatgt    2220
gtgtgttaga ccagactggt ggccatatga aaccaaggtg gctttgttat ttgaagaggc    2280
aggacaggtc gtaaagttag ccttgcgggc actgagggat ttaaccaggg tctggaatag    2340
cgcatcaacc acggcattcc tcatctgctt gataaaagta ttaagaggac aggtcgtgca    2400
aggtgtgata tggctgttac tggtaactgg ggcacaaggc cggctagcct gcaaggaaga    2460
tcacaggtac gctatatcaa caaccaatga gataggcta cttggggccg aaggtctcac    2520
taccacctgg aaagaataca accacaattt gcaactggat gatgggaccg tcaaggccat    2580
ctgcatggca ggttccttta aagtcacagc acttaatgtg gttagtagga gtatctggc    2640 atcattacat aaggacgctt tacccacttc cgtgacattc gagctcctgt tcgacgggac    2700
cagcccattg accgaggaaa tgggagatga cttcgggttc ggactgtgtc cgtatgatac    2760
gagccctgta gtcaagggaa agtacaacac aaccttgttg aatggtagtg cattctacct    2820
agtttgccca atagggtgga cgggtgttat agagtgcacg gcagtgagcc cgacaactct    2880
gagaacagaa gtggtaaaga ccttcagaag agagaaaccc tttccgtaca aagggattg    2940 tgtgaccact acagtggaaa atgaagatct attctactgt aaatgggggg gcaattggac    3000
atgtgtgaaa ggtgaaccag tgacctacac gggggggcca gtaaaacaat gcagatggtg    3060
tggcttcgac ttcaatgagc ctgacggact cccacactac cccataggta agtgcatttt    3120
ggcaaatgag acaggttaca gaatagtgga ttcaacggac tgtaacagag atggcgttgt    3180
aatcagcaca gaggggagtc atgagtgctt gattggtaac acaactgtca aggtgcatgc    3240
attagatgaa agactaggcc ctatgccatg caggcctaag gagatcgtct ctagtgcggg    3300
acctgtaagg aaaacttcct gtacattcaa ctacgcaaaa actctgagga acaggtatta    3360
tgagcccagg gacagctatt tccaacaata tatgctcaag ggcgagtatc agtactggtt    3420
tgatctggat gtgaccgacc gccactcaga ttacttcgca gaattcattg tcttggtggt    3480
ggtggcactg ttgggaggaa gatatgtcct gtggctaata gtgacctaca tagttctaac    3540
agaacaactc gccgctggtc tacagttagg ccagggtgag gtagtgttaa tagggaactt    3600 aatcaccccac acagatattg aggttgtagt atatttctta ctgctctatt tggtcatgag    3660
agatgagcct ataaagaaat ggatactact gctgttccat gctatgacca acaatccagt    3720
taagaccata acagtggcac tgctcatggt tagcggggtt gccaagggtg aaagataga    3780 tggtggttgg cagcggctgc cggagaccaa ctttgatatc caactcgcgc tgacagttat    3840
agtagtcgct gtgatgttgc tggcaaagaa agatccgact accgtcccct tggttataac    3900
ggtggcaacc ctgagaacgg ctaagataac taatggactt agtacagatc tagccatagc    3960
tacagtgtca acagctttgc taacctggac ctacattagt gactattata aatacaagac    4020
cttgctacag taccttatta gcacagtgac aggtatcttc ttgataaggg tactgaaggg    4080
ggtaggtgag ttagatttac acaccccaac cttaccatct tacagacccc tcttcttcat    4140
cctcgtgtac ctcattteca ctgcagtggt aacaagatgg aatctggaca tagccggatt    4200
gctgctgcag tgtgtcccaa ccctttttaat ggttttcacg atgtgggcag acatccttac    4260
```

```
cctgatcctc atactgccta cttacgagtt gacaaaacta tattacctca aggaagtgaa    4320
gattggggca gaaaggggct ggttgtggaa gaccaacttc aagagggtaa atgacatata    4380
cgaagttgac caagctggtg aggggtgta ccttttccca tcaaaacaaa agacaggtac     4440
aataacaggt actatgttgc cattgatcaa agccatactc ataagttgca tcagcaataa    4500
gtggcaattt atatatctat tgtacttgat attcgaagtg tcttactacc ttcacaagaa    4560
gatcatagat gaaatagcag gagggaccaa cttcatctcg agacttgtag ccgctctgat    4620
tgaagccaat tgggcctttg acaacgaaga agttagaggt ttaaagaagt tcttcctgct    4680
gtctagtagg gttaaagaac tgatcatcaa acacaaagtg aggaatgaag tgatggtcca    4740
ctggtttggc gacgaagagg tctatggat gccgaagctg gttggcttag tcaaggcagc     4800
aacactgagt aaaaataaac attgtatttt gtgcaccgtc tgtgaaaaca gagagtggag    4860
aggagaaacc tgcccaaaat gcggccgttt tgggccacca gtgacctgtg catgaccct     4920 agccgacttt gaagaaaaac actataagag gattttcttt agagaggatc aatcagaagg    4980
gccggttagg gaggagtatg cagggtatct gcaatataga gccagagggc aattattcct    5040
gaggaatctc ccggtgctag caacaaaagt caagatgctc ctggtcggaa atcttgggac    5100
ggaggtgggg gatttggaac accttggctg ggtgctcaga gggcctgccg tttgcaagaa    5160
ggttaccgaa catgagaaat gcaccacatc cataatggac aaattaactg ctttcttcgg    5220
tgttatgcca agggggcacca cacctagagc ccctgtgaga ttccccacct ctctcttaaa    5280
gataagaagg gggctggaaa ctggctgggc gtacacacac caaggtggca tcagttcagt    5340
ggaccatgtc acttgtggga aagacttact ggtatgtgac actatgggcc ggacaagggt    5400
tgtttgccaa tcaaataaca agatgacaga cgagtccgag tatggagtta aaactgactc    5460
cggatgcccg gagggagcta ggtgttacgt gttcaaccca gaggcagtta acatatccgg    5520
gactaaagga gccatggtcc acttacaaaa aactggagga gaattcacct gtgtgacagc    5580
atcagggact ccggccttct tgatctcaa gaacctcaaa ggctggtcag gctgccgat     5640 atttgaggca tcaagtggaa gagtagtcgg cagggttaag gtcgggaaga atgaggactc    5700
taaaccaacc aagcttatga gtggaataca aacagtctcc aaaagtacca cagacttgac    5760
agaaatggta aagaaaataa caaccatgaa caggggagaa ttcagacaaa taaccccttgc   5820 cacaggtgcc ggaaaaacca cggaactccc tagatcagtc atagaagaga taggaaggca    5880
taagagggtc ttggtcttga tccctctgag ggcggcagca gagtcagtat accaatatat    5940
gagacaaaaa cacccaagca tagcattcaa cttgaggata ggggagatga aggaagggga    6000
catggccaca gggataaacct atgcctcata tggttacttc tgtcagatgc acaacctaa    6060 gctgcgagcc gcgatggttg agtactcctt catattcctt gatgagtacc actgtgccac    6120
ccccgaacaa ttggctatca tgggaaagat ccacagattt tcagagaacc tgcgggtagt    6180
agccatgacc gcaacaccag caggcacggt aacaactaca gggcaaaaac accctataga    6240
agaatacata gccccagaag tgatgaaggg ggaagactta ggttcagagt acttggacat    6300
agctggacta aagataccag tagaggagat gaagagtaac atgctggtct ttgtgcccac    6360
aaggaacatg gctgtagaga cggcaaagaa actgaaagct aagggttata actcaggcta    6420
ctattatagt ggagaggatc catctaacct gagggtggta acatcacagt ccccgtacgt    6480
ggtggtagca accaacgcaa tagaatcagg tgttactctc ccagacttgg atgtggtcgt    6540
cgacacaggg cttaagtgtg aaaagagat acggctgtca cctaagatgc ccttcatagt    6600
gacgggcctg aagagaatgg ctgtcacgat tgggaacaa gcccagagaa gggggagagt    6660
```

```
tgggagagtg aagcctggga gatactacag gagtcaagaa accccgttg gttccaaaga    6720
ttaccattac gacctactgc aagcacagag gtacggtata gaagatggga taaacatcac    6780
caaatctttt agagagatga attatgattg gagcctttat gaggaggata gtctgatgat    6840
tacacaattg gaaatcctca acaatctgtt gatatcagaa gagctaccaa tggcagtaaa    6900
aaatataatg gccaggactg accacccaga accaatccaa ctggcgtaca acagctacga    6960
aacgcaggtg ccagtgctat tcccaaaaat aaaaaatgga gaggtgactg acagttacga    7020
taactatacc ttcctcaacg caagaaagct ggggatgat gtacctccct acgtgtatgc     7080
cacagaggat gaggacttag cggtagagct gctgggctta gactggccgg accctgggaa    7140
ccaaggaacc gtggaggctg gtagagcact aaaacaagta gttggtctat caacagctga    7200
gaacgccctg ttagtagctt tattcggcta tgtaggatat caggcactct caaagaggca    7260
tataccagta gtcacagaca tatattcaat tgaagatcac aggttggaag acaccacaca    7320
cctacagtat gccccgaatg ctatcaagac ggaggggaag gagacagaat tgaaggagct    7380
agctcagggg gatgtgcaga gatgtatgga agctatgact aattatgcaa gagatggcat    7440
ccaattcatg aagtctcagg cactgaaagt gaaagaaacc cccacttaca aagagacaat    7500
ggacaccgtg gcggactatg taaagaagtt catggaggca ctggcggaca gcaaagaaga    7560
catcataaaa tatgggttgt ggggggacgca cacaacctta tataagagca tcggtgctag    7620
gcttgggaac gagactgcgt tcgctaccct ggtcgtgaaa tggctggcat ttgggggaga    7680
atcaatagca gaccatgtca acaagcggc cacagacttg gtcgtttact atatcatcaa    7740
cagacctcag ttcccaggag acacggagac acaacaggaa ggaaggaaat tgtagccag    7800
cctactggtc tcagccctgg ctacttacac ttacaaaagc tggaattaca ataatctgtc    7860
caagatagtt gaaccggctt tggctactct gccctatgcc gccacagctc tcaagctatt    7920
cgcccccact cgattggaga gcgttgtcat actgagtacc gcaatctaca aaacctacct    7980
atcaatcagg cgcggaaaaa gcgatggttt gctaggcaca ggggttagtg cggctatgga    8040
aatcatgtca caaaacccag tatctgtggg tatagcggtc atgctagggg tggggccgt    8100
agcggcccac aatgcaatcg aagccagtga gcagaagaga acactactca tgaaagtttt    8160
tgtaaagaac ttcttggatc aggcagccac tgatgaatta gtcaaggaga gccctgagaa    8220
aataataatg gctttgtttg aagcagtgca gacagtcggc aaccctctta gactggtata    8280
ccacctttac ggagttttt acaaagggtg ggaggcaaaa gagttggccc aaaggacagc    8340
cggtaggaat ctttttcactt tgataatgtt tgaggctgtg gaactactgg gagtagatag    8400
cgaaggaaag atccgccagc tatcaagcaa ttacatacta gagctcctgt ataagttccg    8460
tgacagtatc aagtccagcg tgaggcagat ggcaatcagc tgggcccctg ccccttttag    8520
ttgtgattgg acaccgacgg atgacagaat agggcttccc caagataatt tcctccgagt    8580
ggagacaaaa tgcccctgtg gttacaagat gaaagcagtt aagaattgtg ctggggagtt    8640
gagactctta aagaggaag gctcatttct ctgcaggaat aaattcggga gaggttcacg    8700
gaactacagg gtgacaaaat actatgatga caatctatca gaaataaagc cagtgataag    8760
aatggaagga catgtggaac tctactacaa gggagccact attaaactgg atttcaacaa    8820
cagtaaaaca atattggcaa ccgataaatg ggaggtcgat cactccactc tggtcagggt    8880
gctcaagagg cacacagggg ctggatatcg tgggcatac ctgggtgaga aaccgaacca     8940
caaacatctg ataagagggg actgcgcaac catcaccaaa gataaggttt gttttctcaa    9000
gatgaagaga gggtgtgcat ttacttatga cttatcccct cacaacctta cccggctgat    9060
```

```
cgaattggta cacaagaata acttggaaga caaagagatt cctgccgtta cggtcacaac   9120
ctggctggct tacacatttg taaatgaaga tatagggacc ataaaaccag ccttcgggga   9180
gaaaataaca ccagagatgc aggaggagat aaccttgcag cctgctgtag tggtggatgc   9240
aactgacgtg accgtgaccg tggtagggga aacccctact atgactacag gggagacccc   9300
aacaacgttc accagctcag gtccagaccc gaaaggccaa caagttttaa aactgggagt   9360
aggtgaaggc caatacccog ggactaatcc acagagagca agcctgcacg aagccataca   9420
aagcgcagat gaaaggccct ctgtgttgat attggggtct gataaagcca cctctaatag   9480
agtgaaaact gtaaagaatg tgaaggtata cagaggcagg gacccactag aagtgagaga   9540
tatgatgagg aggggaaaga tcctagtcat agccctgtct agggttgata atgctctatt   9600
gaaatttgta gattacaaag gcacctttct aactagagag accctggagg cattaagttt   9660
gggtaggcca aaaagaaaa acataaccaa ggcagaagca cagtggttgc tgcgcctcga   9720
agaccaaatg gaagagctac ccgattggtt cgcagccggg gaacccatt ttttagaggc     9780 caatattaaa catgacaggt atcatctggt agggatata gctactatca aagagaaagc      9840
caaacaattg ggggctacag actctacaaa gatatccaag gaggttggtg caaaagtata   9900
ttctatgaaa ttgagtaatt gggtgatgca agaagaaaac aaacagagca acttgacccc    9960
cttatttgaa gagctcctac agcagtgtcc acccggaggc caaaacaaaa ctgcacatat   10020
ggtctctgct taccaactag ctcaagggaa ctggatgcca accagctgcc atgtttttat   10080
ggggaccata tctgccagaa ggactaagac ccatccatat gaagcatatg tcaagttaag   10140
ggagttggta gaggaacaca agatgaaaac attgtgtccc ggatcaagtc tgcgtaagca   10200
caatgaatgg gtaattggca agatcaaata ccagggcaac ctgaggacca aacacatgtt   10260
gaaccccggc aaggtggcag agcaactgca cagagaagga cacagacaca atgtgtataa   10320
caagacaata ggctcagtga tgacagctac tggcatcagg ttggagaagt tgcccgtggt    10380
tagggcccag acagacacaa ccaacttcca ccaagcaata agggataaga tagacaagga    10440
agagaatcta cagaccccgg gtttacataa gaaactaatg gaagttttca atgcattgaa    10500
acgacccgag ttagagtcct cctatgacgc tgtggaatgg gaggaattgg agagaggaat    10560
aaacagaaag ggtgctgctg gtttctttga acgcaaaaac ataggggaga tattggattc    10620
agagaaaaat aaagtagaag agattattga caatctgaaa aagggtagaa atatcaaata    10680
ctatgaaacc gcaatcccaa aaaatgaaaa gagggatgtc aatgatgact ggaccgcagg   10740
tgactttgtg gacgagaaga aacccagagt catacaatac cctgaagcaa aaacaaggct     10800
ggccatcacc aaggtgatgt ataagtgggt gaagcagaag ccagtagtca tacccggta     10860 tgaagggaag acacctctgt tccaaatttt tgacaaagta aagaaggaat gggatcaatt    10920
ccaaaatcca gtggcagtga gcttcgacac taaggcgtgg gacacccagg tgaccacaaa    10980
tgatctggag ctgataaagg acatacaaaa gtactacttc aagaagaaat ggcataaatt    11040
tattgacacc ctgactatgc atatgtcaga agtacccgta atcactgctg atggggaggt    11100
gtatataagg aaagggcaaa gaggtagtgg acagcccgac acaagcgcag gcaacagcat   11160
gctaaatgtg ttaacaatgg tttatgcctt ctgcgaggcc acaggggtac cctacaagag    11220 tttttgacagg gtgcaaaaaa ttcatgtgtg cggggacgat ggtttcctga tcacagagag    11280
agctctcggc gagaaattcg caagcaaggg agtccaaatc ctgtatgaag ctgggaagcc   11340
ccagaagatc actgaagggg acaaaatgaa agtggcctac caatttgatg atattgagtt    11400
ttgctcccat acaccaatac aagtaaggtg gtcagataac acttctagct acatgccagg    11460
```

```
gagaaataca accacaatcc tggctaaaat ggccacaagg ttagattcca gtggtgagag    11520
gggtaccata gcgtacgaga aagcagtagc attcagcttc ctgctaatgt attcctggaa    11580
cccactaatc agaaggattt gcttattggt actatcaact gaactgcaag tgaaaccagg    11640
gaagtcaacc acttactatt atgaagggga cccgatatct gcctacaagg aagtcatcgg    11700
ccacaatctt ttcgatctca agagaacaag cttcgagaag ctggccaagt taaatctcag    11760
catgtccgta ctcggggcct ggactagaca caccagcaaa agactactac aagactgtgt    11820
caatatgggt gttaaagagg gcaactggtt agtcaatgca gacagactgg tgagtagtaa    11880
gactggaaat aggtatgtac ctggagaagg ccacaccctg caagggagac attatgaaga    11940
actggtgttg gcaagaaaac agatcaacag cttccaaggg acagacaggt acaatctagg    12000
cccaatagtc aacatggtgt taaggaggct gagagtcatg atgatgaccc tgataggag    12060 aggggtatga gtgcgggtga cccgcgatct ggaccgtca gtaggaccct attgtagata    12120
acactaattt tttatttatt tagatattac tatttattta tttatttatt tattgaatga    12180
gtaagaactg gtacaaacta cctcatgtta ccacactaca ctcattttaa cagcacttta    12240
gctggaagga aaattcctga cgtccacagt tggactaagg taatttccta acggccc      12297
```

<210> SEQ ID NO 3
<211> LENGTH: 3898
<212> TYPE: PRT
<213> ORGANISM: Classical Swine Fever Virus

<400> SEQUENCE: 3

```
Met Glu Leu Asn His Phe Glu Leu Leu Tyr Lys Thr Asn Lys Gln Lys
1               5                   10                  15

Pro Met Gly Val Glu Glu Pro Val Tyr Asp Val Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Arg Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Leu Thr Asp
145                 150                 155                 160

Cys Pro Leu Trp Val Thr Ser Cys Ser Asp Asp Gly Ala Ser Ala Ser
                165                 170                 175

Lys Glu Lys Lys Pro Asp Arg Ile Asn Lys Gly Lys Leu Lys Ile Ala
            180                 185                 190

Pro Lys Glu His Glu Lys Asp Ser Arg Thr Lys Pro Pro Asp Ala Thr
        195                 200                 205

Ile Val Val Glu Gly Val Lys Tyr Gln Val Lys Lys Gly Lys Val
    210                 215                 220

Lys Gly Lys Asn Thr Gln Asp Gly Leu Tyr His Asn Lys Asn Lys Pro
```

```
                225                 230                 235                 240
Pro Glu Ser Arg Lys Lys Leu Glu Lys Ala Leu Leu Ala Trp Ala Val
                    245                 250                 255
Ile Ala Ile Met Leu Tyr Gln Pro Val Ala Ala Glu Asn Ile Thr Gln
                260                 265                 270
Trp Asn Leu Ser Asp Asn Gly Thr Asn Gly Ile Gln His Ala Met Tyr
            275                 280                 285
Leu Arg Gly Val Ser Arg Ser Leu His Gly Ile Trp Pro Glu Lys Ile
        290                 295                 300
Cys Lys Gly Val Pro Thr Tyr Leu Ala Thr Asp Thr Glu Leu Arg Glu
305                 310                 315                 320
Ile Gln Gly Met Met Asp Ala Ser Glu Gly Thr Asn Tyr Thr Cys Cys
                    325                 330                 335
Lys Leu Gln Arg His Glu Trp Asn Lys His Gly Trp Cys Asn Trp Tyr
                340                 345                 350
Asn Ile Asp Pro Trp Ile Gln Leu Met Asn Arg Thr Gln Ala Asn Leu
            355                 360                 365
Ala Glu Gly Pro Pro Ser Lys Glu Cys Ala Val Thr Cys Arg Tyr Asp
        370                 375                 380
Lys Asn Ala Asp Ile Asn Val Val Thr Gln Ala Arg Asn Arg Pro Thr
385                 390                 395                 400
Thr Leu Thr Gly Cys Lys Lys Gly Lys Asn Phe Ser Phe Ala Gly Thr
                    405                 410                 415
Val Ile Glu Gly Pro Cys Asn Phe Asn Val Ser Val Gly Asp Ile Leu
                420                 425                 430
Tyr Gly Asp His Glu Cys Gly Ser Leu Leu Gln Asp Thr Ala Leu Tyr
            435                 440                 445
Leu Val Asp Gly Met Thr Asn Thr Ile Glu Arg Ala Arg Gln Gly Ala
        450                 455                 460
Ala Arg Val Thr Ser Trp Leu Gly Arg Gln Leu Arg Thr Ala Gly Lys
465                 470                 475                 480
Arg Leu Glu Gly Arg Ser Lys Thr Trp Phe Gly Ala Tyr Ala Leu Ser
                    485                 490                 495
Pro Tyr Cys Ala Val Thr Ser Lys Ile Gly Tyr Ile Trp Tyr Thr Asn
                500                 505                 510
Ala Cys Thr Pro Ala Cys Leu Pro Lys Asn Thr Lys Ile Ile Gly Pro
            515                 520                 525
Gly Lys Phe Asp Thr Asn Ala Glu Asp Gly Lys Ile Leu His Glu Met
        530                 535                 540
Gly Gly His Leu Ser Glu Phe Leu Leu Leu Ser Leu Val Val Leu Ser
545                 550                 555                 560
Asp Phe Ala Pro Glu Thr Ala Ser Ala Leu Tyr Leu Ile Leu His Tyr
                    565                 570                 575
Val Ile Pro Gln Ser His Glu Glu Pro Glu Gly Cys Asp Thr Asn Gln
                580                 585                 590
Leu Asn Leu Thr Val Glu Leu Arg Thr Glu Asp Val Ile Pro Ser Ser
            595                 600                 605
Val Trp Asn Val Gly Lys Tyr Val Cys Val Arg Pro Asp Trp Trp Pro
        610                 615                 620
Tyr Glu Thr Lys Val Ala Leu Leu Phe Glu Glu Ala Gly Gln Val Val
625                 630                 635                 640
Lys Leu Ala Leu Arg Ala Leu Arg Asp Leu Thr Arg Val Trp Asn Ser
                    645                 650                 655
```

```
Ala Ser Thr Thr Ala Phe Leu Ile Cys Leu Ile Lys Val Leu Arg Gly
            660                 665                 670

Gln Val Val Gln Gly Val Ile Trp Leu Leu Val Thr Gly Ala Gln
        675                 680                 685

Gly Arg Leu Ala Cys Lys Glu Asp His Arg Tyr Ala Ile Ser Thr Thr
690                 695                 700

Asn Glu Ile Gly Leu Leu Gly Ala Glu Gly Leu Thr Thr Thr Trp Lys
705                 710                 715                 720

Glu Tyr Asn His Asn Leu Gln Leu Asp Asp Gly Thr Val Lys Ala Ile
                725                 730                 735

Cys Met Ala Gly Ser Phe Lys Val Thr Ala Leu Asn Val Val Ser Arg
            740                 745                 750

Arg Tyr Leu Ala Ser Leu His Lys Asp Ala Leu Pro Thr Ser Val Thr
        755                 760                 765

Phe Glu Leu Leu Phe Asp Gly Thr Ser Pro Leu Thr Glu Glu Met Gly
770                 775                 780

Asp Asp Phe Gly Phe Gly Leu Cys Pro Tyr Asp Thr Ser Pro Val Val
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Ile Glu Cys Thr Ala Val Ser
            820                 825                 830

Pro Thr Thr Leu Arg Thr Glu Val Val Lys Thr Phe Arg Arg Glu Lys
        835                 840                 845

Pro Phe Pro Tyr Arg Arg Asp Cys Val Thr Thr Thr Val Glu Asn Glu
850                 855                 860

Asp Leu Phe Tyr Cys Lys Trp Gly Gly Asn Trp Thr Cys Val Lys Gly
865                 870                 875                 880

Glu Pro Val Thr Tyr Thr Gly Gly Pro Val Lys Gln Cys Arg Trp Cys
                885                 890                 895

Gly Phe Asp Phe Asn Glu Pro Asp Gly Leu Pro His Tyr Pro Ile Gly
            900                 905                 910

Lys Cys Ile Leu Ala Asn Glu Thr Gly Tyr Arg Ile Val Asp Ser Thr
        915                 920                 925

Asp Cys Asn Arg Asp Gly Val Val Ile Ser Thr Glu Gly Ser His Glu
930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Ala Gly
                965                 970                 975

Pro Val Arg Lys Thr Ser Cys Thr Phe Asn Tyr Ala Lys Thr Leu Arg
            980                 985                 990

Asn Arg Tyr Tyr Glu Pro Arg Asp Ser Tyr Phe Gln Gln Tyr Met Leu
        995                 1000                1005

Lys Gly Glu Tyr Gln Tyr Trp Phe Asp Leu Asp Val Thr Asp Arg
        1010                1015                1020

His Ser Asp Tyr Phe Ala Glu Phe Ile Val Leu Val Val Val Ala
        1025                1030                1035

Leu Leu Gly Gly Arg Tyr Val Leu Trp Leu Ile Val Thr Tyr Ile
        1040                1045                1050

Val Leu Thr Glu Gln Leu Ala Ala Gly Leu Gln Leu Gly Gln Gly
        1055                1060                1065

Glu Val Val Leu Ile Gly Asn Leu Ile Thr His Thr Asp Ile Glu
        1070                1075                1080
```

-continued

```
Val Val Val Tyr Phe Leu Leu Leu Tyr Leu Val Met Arg Asp Glu
    1085                1090                1095

Pro Ile Lys Lys Trp Ile Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Lys Gly Gly Lys Ile Asp Gly Gly Trp Gln Arg Leu Pro
    1130                1135                1140

Glu Thr Asn Phe Asp Ile Gln Leu Ala Leu Thr Val Ile Val Val
    1145                1150                1155

Ala Val Met Leu Leu Ala Lys Lys Asp Pro Thr Thr Val Pro Leu
    1160                1165                1170

Val Ile Thr Val Ala Thr Leu Arg Thr Ala Lys Ile Thr Asn Gly
    1175                1180                1185

Leu Ser Thr Asp Leu Ala Ile Ala Thr Val Ser Thr Ala Leu Leu
    1190                1195                1200

Thr Trp Thr Tyr Ile Ser Asp Tyr Tyr Lys Tyr Lys Thr Leu Leu
    1205                1210                1215

Gln Tyr Leu Ile Ser Thr Val Thr Gly Ile Phe Leu Ile Arg Val
    1220                1225                1230

Leu Lys Gly Val Gly Glu Leu Asp Leu His Thr Pro Thr Leu Pro
    1235                1240                1245

Ser Tyr Arg Pro Leu Phe Phe Ile Leu Val Tyr Leu Ile Ser Thr
    1250                1255                1260

Ala Val Val Thr Arg Trp Asn Leu Asp Ile Ala Gly Leu Leu Leu
    1265                1270                1275

Gln Cys Val Pro Thr Leu Leu Met Val Phe Thr Met Trp Ala Asp
    1280                1285                1290

Ile Leu Thr Leu Ile Leu Ile Leu Pro Thr Tyr Glu Leu Thr Lys
    1295                1300                1305

Leu Tyr Tyr Leu Lys Glu Val Lys Ile Gly Ala Glu Arg Gly Trp
    1310                1315                1320

Leu Trp Lys Thr Asn Phe Lys Arg Val Asn Asp Ile Tyr Glu Val
    1325                1330                1335

Asp Gln Ala Gly Glu Gly Val Tyr Leu Phe Pro Ser Lys Gln Lys
    1340                1345                1350

Thr Gly Thr Ile Thr Gly Thr Met Leu Pro Leu Ile Lys Ala Ile
    1355                1360                1365

Leu Ile Ser Cys Ile Ser Asn Lys Trp Gln Phe Ile Tyr Leu Leu
    1370                1375                1380

Tyr Leu Ile Phe Glu Val Ser Tyr Tyr Leu His Lys Lys Ile Ile
    1385                1390                1395

Asp Glu Ile Ala Gly Gly Thr Asn Phe Ile Ser Arg Leu Val Ala
    1400                1405                1410

Ala Leu Ile Glu Ala Asn Trp Ala Phe Asp Asn Glu Glu Val Arg
    1415                1420                1425

Gly Leu Lys Lys Phe Phe Leu Leu Ser Ser Arg Val Lys Glu Leu
    1430                1435                1440

Ile Ile Lys His Lys Val Arg Asn Glu Val Met Val His Trp Phe
    1445                1450                1455

Gly Asp Glu Glu Val Tyr Gly Met Pro Lys Leu Val Gly Leu Val
    1460                1465                1470

Lys Ala Ala Thr Leu Ser Lys Asn Lys His Cys Ile Leu Cys Thr
```

```
                1475                1480                1485

Val Cys Glu Asn Arg Glu Trp Arg Gly Glu Thr Cys Pro Lys Cys
    1490                1495                1500

Gly Arg Phe Gly Pro Pro Val Thr Cys Gly Met Thr Leu Ala Asp
    1505                1510                1515

Phe Glu Glu Lys His Tyr Lys Arg Ile Phe Phe Arg Glu Asp Gln
    1520                1525                1530

Ser Glu Gly Pro Val Arg Glu Tyr Ala Gly Tyr Leu Gln Tyr
    1535                1540                1545

Arg Ala Arg Gly Gln Leu Phe Leu Arg Asn Leu Pro Val Leu Ala
    1550                1555                1560

Thr Lys Val Lys Met Leu Leu Val Gly Asn Leu Gly Thr Glu Val
    1565                1570                1575

Gly Asp Leu Glu His Leu Gly Trp Val Leu Arg Gly Pro Ala Val
    1580                1585                1590

Cys Lys Lys Val Thr Glu His Glu Lys Cys Thr Thr Ser Ile Met
    1595                1600                1605

Asp Lys Leu Thr Ala Phe Phe Gly Val Met Pro Arg Gly Thr Thr
    1610                1615                1620

Pro Arg Ala Pro Val Arg Phe Pro Thr Ser Leu Leu Lys Ile Arg
    1625                1630                1635

Arg Gly Leu Glu Thr Gly Trp Ala Tyr Thr His Gln Gly Gly Ile
    1640                1645                1650

Ser Ser Val Asp His Val Thr Cys Gly Lys Asp Leu Leu Val Cys
    1655                1660                1665

Asp Thr Met Gly Arg Thr Arg Val Val Cys Gln Ser Asn Asn Lys
    1670                1675                1680

Met Thr Asp Glu Ser Glu Tyr Gly Val Lys Thr Asp Ser Gly Cys
    1685                1690                1695

Pro Glu Gly Ala Arg Cys Tyr Val Phe Asn Pro Glu Ala Val Asn
    1700                1705                1710

Ile Ser Gly Thr Lys Gly Ala Met Val His Leu Gln Lys Thr Gly
    1715                1720                1725

Gly Glu Phe Thr Cys Val Thr Ala Ser Gly Thr Pro Ala Phe Phe
    1730                1735                1740

Asp Leu Lys Asn Leu Lys Gly Trp Ser Gly Leu Pro Ile Phe Glu
    1745                1750                1755

Ala Ser Ser Gly Arg Val Val Gly Arg Val Lys Val Gly Lys Asn
    1760                1765                1770

Glu Asp Ser Lys Pro Thr Lys Leu Met Ser Gly Ile Gln Thr Val
    1775                1780                1785

Ser Lys Ser Thr Thr Asp Leu Thr Glu Met Val Lys Lys Ile Thr
    1790                1795                1800

Thr Met Asn Arg Gly Glu Phe Arg Gln Ile Thr Leu Ala Thr Gly
    1805                1810                1815

Ala Gly Lys Thr Thr Glu Leu Pro Arg Ser Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Gln Lys His Pro Ser Ile
    1850                1855                1860

Ala Phe Asn Leu Arg Ile Gly Glu Met Lys Glu Gly Asp Met Ala
    1865                1870                1875
```

-continued

```
Thr Gly Ile Thr Tyr Ala Ser Tyr Gly Tyr Phe Cys Gln Met Pro
    1880            1885            1890

Gln Pro Lys Leu Arg Ala Ala Met Val Glu Tyr Ser Phe Ile Phe
    1895            1900            1905

Leu Asp Glu Tyr His Cys Ala Thr Pro Glu Gln Leu Ala Ile Met
    1910            1915            1920

Gly Lys Ile His Arg Phe Ser Glu Asn Leu Arg Val Val Ala Met
    1925            1930            1935

Thr Ala Thr Pro Ala Gly Thr Val Thr Thr Gly Gln Lys His
    1940            1945            1950

Pro Ile Glu Glu Tyr Ile Ala Pro Glu Val Met Lys Gly Glu Asp
    1955            1960            1965

Leu Gly Ser Glu Tyr Leu Asp Ile Ala Gly Leu Lys Ile Pro Val
    1970            1975            1980

Glu Glu Met Lys Ser Asn Met Leu Val Phe Val Pro Thr Arg Asn
    1985            1990            1995

Met Ala Val Glu Thr Ala Lys Lys Leu Lys Ala Lys Gly Tyr Asn
    2000            2005            2010

Ser Gly Tyr Tyr Tyr Ser Gly Glu Asp Pro Ser Asn Leu Arg Val
    2015            2020            2025

Val Thr Ser Gln Ser Pro Tyr Val Val Val Ala Thr Asn Ala Ile
    2030            2035            2040

Glu Ser Gly Val Thr Leu Pro Asp Leu Asp Val Val Val Asp Thr
    2045            2050            2055

Gly Leu Lys Cys Glu Lys Arg Ile Arg Leu Ser Pro Lys Met Pro
    2060            2065            2070

Phe Ile Val Thr Gly Leu Lys Arg Met Ala Val Thr Ile Gly Glu
    2075            2080            2085

Gln Ala Gln Arg Arg Gly Arg Val Gly Arg Val Lys Pro Gly Arg
    2090            2095            2100

Tyr Tyr Arg Ser Gln Glu Thr Pro Val Gly Ser Lys Asp Tyr His
    2105            2110            2115

Tyr Asp Leu Leu Gln Ala Gln Arg Tyr Gly Ile Glu Asp Gly Ile
    2120            2125            2130

Asn Ile Thr Lys Ser Phe Arg Glu Met Asn Tyr Asp Trp Ser Leu
    2135            2140            2145

Tyr Glu Glu Asp Ser Leu Met Ile Thr Gln Leu Glu Ile Leu Asn
    2150            2155            2160

Asn Leu Leu Ile Ser Glu Glu Leu Pro Met Ala Val Lys Asn Ile
    2165            2170            2175

Met Ala Arg Thr Asp His Pro Glu Pro Ile Gln Leu Ala Tyr Asn
    2180            2185            2190

Ser Tyr Glu Thr Gln Val Pro Val Leu Phe Pro Lys Ile Lys Asn
    2195            2200            2205

Gly Glu Val Thr Asp Ser Tyr Asp Asn Tyr Thr Phe Leu Asn Ala
    2210            2215            2220

Arg Lys Leu Gly Asp Asp Val Pro Pro Tyr Val Tyr Ala Thr Glu
    2225            2230            2235

Asp Glu Asp Leu Ala Val Glu Leu Leu Gly Leu Asp Trp Pro Asp
    2240            2245            2250

Pro Gly Asn Gln Gly Thr Val Glu Ala Gly Arg Ala Leu Lys Gln
    2255            2260            2265

Val Val Gly Leu Ser Thr Ala Glu Asn Ala Leu Leu Val Ala Leu
    2270            2275            2280
```

-continued

```
Phe Gly Tyr Val Gly Tyr Gln Ala Leu Ser Lys Arg His Ile Pro
    2285              2290                2295
Val Val Thr Asp Ile Tyr Ser Ile Glu Asp His Arg Leu Glu Asp
    2300              2305                2310
Thr Thr His Leu Gln Tyr Ala Pro Asn Ala Ile Lys Thr Glu Gly
    2315              2320                2325
Lys Glu Thr Glu Leu Lys Glu Leu Ala Gln Gly Asp Val Gln Arg
    2330              2335                2340
Cys Met Glu Ala Met Thr Asn Tyr Ala Arg Asp Gly Ile Gln Phe
    2345              2350                2355
Met Lys Ser Gln Ala Leu Lys Val Lys Glu Thr Pro Thr Tyr Lys
    2360              2365                2370
Glu Thr Met Asp Thr Val Ala Asp Tyr Val Lys Lys Phe Met Glu
    2375              2380                2385
Ala Leu Ala Asp Ser Lys Glu Asp Ile Ile Lys Tyr Gly Leu Trp
    2390              2395                2400
Gly Thr His Thr Thr Leu Tyr Lys Ser Ile Gly Ala Arg Leu Gly
    2405              2410                2415
Asn Glu Thr Ala Phe Ala Thr Leu Val Val Lys Trp Leu Ala Phe
    2420              2425                2430
Gly Gly Glu Ser Ile Ala Asp His Val Lys Gln Ala Ala Thr Asp
    2435              2440                2445
Leu Val Val Tyr Tyr Ile Ile Asn Arg Pro Gln Phe Pro Gly Asp
    2450              2455                2460
Thr Glu Thr Gln Gln Glu Gly Arg Lys Phe Val Ala Ser Leu Leu
    2465              2470                2475
Val Ser Ala Leu Ala Thr Tyr Thr Tyr Lys Ser Trp Asn Tyr Asn
    2480              2485                2490
Asn Leu Ser Lys Ile Val Glu Pro Ala Leu Ala Thr Leu Pro Tyr
    2495              2500                2505
Ala Ala Thr Ala Leu Lys Leu Phe Ala Pro Thr Arg Leu Glu Ser
    2510              2515                2520
Val Val Ile Leu Ser Thr Ala Ile Tyr Lys Thr Tyr Leu Ser Ile
    2525              2530                2535
Arg Arg Gly Lys Ser Asp Gly Leu Leu Gly Thr Gly Val Ser Ala
    2540              2545                2550
Ala Met Glu Ile Met Ser Gln Asn Pro Val Ser Val Gly Ile Ala
    2555              2560                2565
Val Met Leu Gly Val Gly Ala Val Ala Ala His Asn Ala Ile Glu
    2570              2575                2580
Ala Ser Glu Gln Lys Arg Thr Leu Leu Met Lys Val Phe Val Lys
    2585              2590                2595
Asn Phe Leu Asp Gln Ala Ala Thr Asp Glu Leu Val Lys Glu Ser
    2600              2605                2610
Pro Glu Lys Ile Ile Met Ala Leu Phe Glu Ala Val Gln Thr Val
    2615              2620                2625
Gly Asn Pro Leu Arg Leu Val Tyr His Leu Tyr Gly Val Phe Tyr
    2630              2635                2640
Lys Gly Trp Glu Ala Lys Glu Leu Ala Gln Arg Thr Ala Gly Arg
    2645              2650                2655
Asn Leu Phe Thr Leu Ile Met Phe Glu Ala Val Glu Leu Leu Gly
    2660              2665                2670
Val Asp Ser Glu Gly Lys Ile Arg Gln Leu Ser Ser Asn Tyr Ile
```

-continued

```
                2675                2680                2685

Leu Glu Leu Leu Tyr Lys Phe Arg Asp Ser Ile Lys Ser Ser Val
    2690                2695                2700

Arg Gln Met Ala Ile Ser Trp Ala Pro Ala Pro Phe Ser Cys Asp
    2705                2710                2715

Trp Thr Pro Thr Asp Asp Arg Ile Gly Leu Pro Gln Asp Asn Phe
    2720                2725                2730

Leu Arg Val Glu Thr Lys Cys Pro Cys Gly Tyr Lys Met Lys Ala
    2735                2740                2745

Val Lys Asn Cys Ala Gly Glu Leu Arg Leu Leu Glu Glu Glu Gly
    2750                2755                2760

Ser Phe Leu Cys Arg Asn Lys Phe Gly Arg Gly Ser Arg Asn Tyr
    2765                2770                2775

Arg Val Thr Lys Tyr Tyr Asp Asp Asn Leu Ser Glu Ile Lys Pro
    2780                2785                2790

Val Ile Arg Met Glu Gly His Val Glu Leu Tyr Tyr Lys Gly Ala
    2795                2800                2805

Thr Ile Lys Leu Asp Phe Asn Asn Ser Lys Thr Ile Leu Ala Thr
    2810                2815                2820

Asp Lys Trp Glu Val Asp His Ser Thr Leu Val Arg Val Leu Lys
    2825                2830                2835

Arg His Thr Gly Ala Gly Tyr Arg Gly Ala Tyr Leu Gly Glu Lys
    2840                2845                2850

Pro Asn His Lys His Leu Ile Glu Arg Asp Cys Ala Thr Ile Thr
    2855                2860                2865

Lys Asp Lys Val Cys Phe Leu Lys Met Lys Arg Gly Cys Ala Phe
    2870                2875                2880

Thr Tyr Asp Leu Ser Leu His Asn Leu Thr Arg Leu Ile Glu Leu
    2885                2890                2895

Val His Lys Asn Asn Leu Glu Asp Lys Glu Ile Pro Ala Val Thr
    2900                2905                2910

Val Thr Thr Trp Leu Ala Tyr Thr Phe Val Asn Glu Asp Ile Gly
    2915                2920                2925

Thr Ile Lys Pro Ala Phe Gly Glu Lys Ile Thr Pro Glu Met Gln
    2930                2935                2940

Glu Glu Ile Thr Leu Gln Pro Ala Val Val Val Asp Ala Thr Asp
    2945                2950                2955

Val Thr Val Thr Val Val Gly Glu Thr Pro Thr Met Thr Thr Gly
    2960                2965                2970

Glu Thr Pro Thr Thr Phe Thr Ser Ser Gly Pro Asp Pro Lys Gly
    2975                2980                2985

Gln Gln Val Leu Lys Leu Gly Val Gly Glu Gly Gln Tyr Pro Gly
    2990                2995                3000

Thr Asn Pro Gln Arg Ala Ser Leu His Glu Ala Ile Gln Ser Ala
    3005                3010                3015

Asp Glu Arg Pro Ser Val Leu Ile Leu Gly Ser Asp Lys Ala Thr
    3020                3025                3030

Ser Asn Arg Val Lys Thr Val Lys Asn Val Lys Val Tyr Arg Gly
    3035                3040                3045

Arg Asp Pro Leu Glu Val Arg Asp Met Met Arg Arg Gly Lys Ile
    3050                3055                3060

Leu Val Ile Ala Leu Ser Arg Val Asp Asn Ala Leu Leu Lys Phe
    3065                3070                3075
```

```
Val Asp Tyr Lys Gly Thr Phe Leu Thr Arg Glu Thr Leu Glu Ala
3080                3085                3090

Leu Ser Leu Gly Arg Pro Lys Lys Asn Ile Thr Lys Ala Glu
3095                3100                3105

Ala Gln Trp Leu Leu Arg Leu Glu Asp Gln Met Glu Glu Leu Pro
3110                3115                3120

Asp Trp Phe Ala Ala Gly Glu Pro Ile Phe Leu Glu Ala Asn Ile
3125                3130                3135

Lys His Asp Arg Tyr His Leu Val Gly Asp Ile Ala Thr Ile Lys
3140                3145                3150

Glu Lys Ala Lys Gln Leu Gly Ala Thr Asp Ser Thr Lys Ile Ser
3155                3160                3165

Lys Glu Val Gly Ala Lys Val Tyr Ser Met Lys Leu Ser Asn Trp
3170                3175                3180

Val Met Gln Glu Glu Asn Lys Gln Ser Asn Leu Thr Pro Leu Phe
3185                3190                3195

Glu Glu Leu Leu Gln Gln Cys Pro Pro Gly Gly Gln Asn Lys Thr
3200                3205                3210

Ala His Met Val Ser Ala Tyr Gln Leu Ala Gln Gly Asn Trp Met
3215                3220                3225

Pro Thr Ser Cys His Val Phe Met Gly Thr Ile Ser Ala Arg Arg
3230                3235                3240

Thr Lys Thr His Pro Tyr Glu Ala Tyr Val Lys Leu Arg Glu Leu
3245                3250                3255

Val Glu Glu His Lys Met Lys Thr Leu Cys Pro Gly Ser Ser Leu
3260                3265                3270

Arg Lys His Asn Glu Trp Val Ile Gly Lys Ile Lys Tyr Gln Gly
3275                3280                3285

Asn Leu Arg Thr Lys His Met Leu Asn Pro Gly Lys Val Ala Glu
3290                3295                3300

Gln Leu His Arg Glu Gly His Arg His Asn Val Tyr Asn Lys Thr
3305                3310                3315

Ile Gly Ser Val Met Thr Ala Thr Gly Ile Arg Leu Glu Lys Leu
3320                3325                3330

Pro Val Val Arg Ala Gln Thr Asp Thr Thr Asn Phe His Gln Ala
3335                3340                3345

Ile Arg Asp Lys Ile Asp Lys Glu Glu Asn Leu Gln Thr Pro Gly
3350                3355                3360

Leu His Lys Lys Leu Met Glu Val Phe Asn Ala Leu Lys Arg Pro
3365                3370                3375

Glu Leu Glu Ser Ser Tyr Asp Ala Val Glu Trp Glu Glu Leu Glu
3380                3385                3390

Arg Gly Ile Asn Arg Lys Gly Ala Ala Gly Phe Phe Glu Arg Lys
3395                3400                3405

Asn Ile Gly Glu Ile Leu Asp Ser Glu Lys Asn Lys Val Glu Glu
3410                3415                3420

Ile Ile Asp Asn Leu Lys Lys Gly Arg Asn Ile Lys Tyr Tyr Glu
3425                3430                3435

Thr Ala Ile Pro Lys Asn Glu Lys Arg Asp Val Asn Asp Asp Trp
3440                3445                3450

Thr Ala Gly Asp Phe Val Asp Glu Lys Lys Pro Arg Val Ile Gln
3455                3460                3465

Tyr Pro Glu Ala Lys Thr Arg Leu Ala Ile Thr Lys Val Met Tyr
3470                3475                3480
```

-continued

```
Lys Trp Val Lys Gln Lys Pro Val Val Ile Pro Gly Tyr Glu Gly
3485                3490                3495
Lys Thr Pro Leu Phe Gln Ile Phe Asp Lys Val Lys Lys Glu Trp
3500                3505                3510
Asp Gln Phe Gln Asn Pro Val Ala Val Ser Phe Asp Thr Lys Ala
3515                3520                3525
Trp Asp Thr Gln Val Thr Thr Asn Asp Leu Glu Leu Ile Lys Asp
3530                3535                3540
Ile Gln Lys Tyr Tyr Phe Lys Lys Lys Trp His Lys Phe Ile Asp
3545                3550                3555
Thr Leu Thr Met His Met Ser Glu Val Pro Val Ile Thr Ala Asp
3560                3565                3570
Gly Glu Val Tyr Ile Arg Lys Gly Gln Arg Gly Ser Gly Gln Pro
3575                3580                3585
Asp Thr Ser Ala Gly Asn Ser Met Leu Asn Val Leu Thr Met Val
3590                3595                3600
Tyr Ala Phe Cys Glu Ala Thr Gly Val Pro Tyr Lys Ser Phe Asp
3605                3610                3615
Arg Val Ala Lys Ile His Val Cys Gly Asp Asp Gly Phe Leu Ile
3620                3625                3630
Thr Glu Arg Ala Leu Gly Glu Lys Phe Ala Ser Lys Gly Val Gln
3635                3640                3645
Ile Leu Tyr Glu Ala Gly Lys Pro Gln Lys Ile Thr Glu Gly Asp
3650                3655                3660
Lys Met Lys Val Ala Tyr Gln Phe Asp Asp Ile Glu Phe Cys Ser
3665                3670                3675
His Thr Pro Ile Gln Val Arg Trp Ser Asp Asn Thr Ser Ser Tyr
3680                3685                3690
Met Pro Gly Arg Asn Thr Thr Thr Ile Leu Ala Lys Met Ala Thr
3695                3700                3705
Arg Leu Asp Ser Ser Gly Glu Arg Gly Thr Ile Ala Tyr Glu Lys
3710                3715                3720
Ala Val Ala Phe Ser Phe Leu Leu Met Tyr Ser Trp Asn Pro Leu
3725                3730                3735
Ile Arg Arg Ile Cys Leu Leu Val Leu Ser Thr Glu Leu Gln Val
3740                3745                3750
Lys Pro Gly Lys Ser Thr Thr Tyr Tyr Tyr Glu Gly Asp Pro Ile
3755                3760                3765
Ser Ala Tyr Lys Glu Val Ile Gly His Asn Leu Phe Asp Leu Lys
3770                3775                3780
Arg Thr Ser Phe Glu Lys Leu Ala Lys Leu Asn Leu Ser Met Ser
3785                3790                3795
Val Leu Gly Ala Trp Thr Arg His Thr Ser Lys Arg Leu Leu Gln
3800                3805                3810
Asp Cys Val Asn Met Gly Val Lys Glu Gly Asn Trp Leu Val Asn
3815                3820                3825
Ala Asp Arg Leu Val Ser Ser Lys Thr Gly Asn Arg Tyr Val Pro
3830                3835                3840
Gly Glu Gly His Thr Leu Gln Gly Arg His Tyr Glu Glu Leu Val
3845                3850                3855
Leu Ala Arg Lys Gln Ile Asn Ser Phe Gln Gly Thr Asp Arg Tyr
3860                3865                3870
Asn Leu Gly Pro Ile Val Asn Met Val Leu Arg Arg Leu Arg Val
```

```
                        3875                 3880                  3885
       Met  Met  Met  Thr  Leu  Ile  Gly  Arg  Gly  Val
              3890                  3895

<210> SEQ ID NO 4
<211> LENGTH: 3898
<212> TYPE: PRT
<213> ORGANISM: Classical Swine Fever Virus

<400> SEQUENCE: 4

Met  Glu  Leu  Asn  His  Phe  Glu  Leu  Leu  Tyr  Lys  Thr  Asn  Lys  Gln  Lys
1                  5                   10                  15

Pro  Met  Gly  Val  Glu  Glu  Pro  Val  Tyr  Asp  Val  Thr  Gly  Arg  Pro  Leu
              20                  25                  30

Phe  Gly  Asp  Pro  Ser  Glu  Val  His  Pro  Gln  Ser  Thr  Leu  Lys  Leu  Pro
         35                   40                  45

His  Asp  Arg  Gly  Arg  Gly  Asn  Ile  Lys  Thr  Thr  Leu  Lys  Asn  Leu  Pro
     50                   55                  60

Arg  Arg  Gly  Asp  Cys  Arg  Ser  Gly  Asn  His  Leu  Gly  Pro  Val  Ser  Gly
65                   70                  75                   80

Ile  Tyr  Val  Lys  Pro  Gly  Pro  Val  Phe  Tyr  Gln  Asp  Tyr  Met  Gly  Pro
                 85                  90                  95

Val  Tyr  His  Arg  Ala  Pro  Leu  Glu  Phe  Phe  Asp  Glu  Ala  Gln  Phe  Cys
             100                 105                 110

Glu  Val  Thr  Lys  Arg  Ile  Gly  Arg  Val  Thr  Gly  Ser  Asp  Gly  Lys  Leu
         115                 120                 125

Tyr  His  Ile  Tyr  Val  Cys  Ile  Asp  Gly  Cys  Ile  Leu  Leu  Lys  Leu  Ala
     130                 135                 140

Lys  Arg  Gly  Glu  Pro  Arg  Thr  Leu  Lys  Trp  Ile  Arg  Asn  Leu  Thr  Asp
145                 150                 155                 160

Cys  Pro  Leu  Trp  Val  Thr  Ser  Cys  Ser  Asp  Asp  Gly  Ala  Ser  Ala  Ser
                 165                 170                 175

Lys  Glu  Lys  Lys  Pro  Asp  Arg  Ile  Asn  Lys  Gly  Lys  Leu  Lys  Ile  Ala
             180                 185                 190

Pro  Lys  Glu  His  Glu  Lys  Asp  Ser  Arg  Thr  Lys  Pro  Pro  Asp  Ala  Thr
         195                 200                 205

Ile  Val  Val  Glu  Gly  Val  Lys  Tyr  Gln  Val  Lys  Lys  Lys  Gly  Lys  Val
     210                 215                 220

Lys  Gly  Lys  Asn  Thr  Gln  Asp  Gly  Leu  Tyr  His  Asn  Lys  Asn  Lys  Pro
225                 230                 235                 240

Pro  Glu  Ser  Arg  Lys  Lys  Leu  Glu  Lys  Ala  Leu  Leu  Ala  Trp  Ala  Val
                 245                 250                 255

Ile  Ala  Ile  Met  Leu  Tyr  Gln  Pro  Val  Ala  Ala  Glu  Asn  Ile  Thr  Gln
             260                 265                 270

Trp  Asn  Leu  Ser  Asp  Asn  Gly  Thr  Asn  Gly  Ile  Gln  His  Ala  Met  Tyr
         275                 280                 285

Leu  Arg  Gly  Val  Ser  Arg  Ser  Leu  His  Gly  Ile  Trp  Pro  Glu  Lys  Ile
     290                 295                 300

Cys  Lys  Gly  Val  Pro  Thr  Tyr  Leu  Ala  Thr  Asp  Thr  Glu  Leu  Arg  Glu
305                 310                 315                 320

Ile  Gln  Gly  Met  Met  Asp  Ala  Ser  Glu  Gly  Thr  Asn  Tyr  Thr  Cys  Cys
                 325                 330                 335

Lys  Leu  Gln  Arg  His  Glu  Trp  Asn  Lys  His  Gly  Trp  Cys  Asn  Trp  Tyr
             340                 345                 350

Asn  Ile  Asp  Pro  Trp  Ile  Gln  Leu  Met  Asn  Arg  Thr  Gln  Ala  Asn  Leu
```

```
                355                 360                 365
Ala Glu Gly Pro Pro Ser Lys Glu Cys Ala Val Thr Cys Arg Tyr Asp
370                 375                 380

Lys Asn Ala Asp Ile Asn Val Val Thr Gln Ala Arg Asn Arg Pro Thr
385                 390                 395                 400

Thr Leu Thr Gly Cys Lys Lys Gly Lys Asn Phe Ser Phe Ala Gly Thr
                405                 410                 415

Val Ile Glu Gly Pro Cys Asn Phe Asn Val Ser Val Glu Asp Ile Leu
                420                 425                 430

Tyr Gly Asp His Glu Cys Gly Ser Leu Leu Gln Asp Thr Ala Leu Tyr
                435                 440                 445

Leu Val Asp Gly Met Thr Asn Thr Ile Glu Arg Ala Arg Gln Gly Ala
            450                 455                 460

Ala Arg Val Thr Ser Trp Leu Gly Arg Gln Leu Arg Thr Ala Gly Lys
465                 470                 475                 480

Arg Leu Glu Gly Arg Ser Lys Thr Trp Phe Gly Ala Tyr Ala Leu Ser
                485                 490                 495

Pro Tyr Cys Asn Val Thr Ser Lys Ile Gly Tyr Ile Trp Tyr Thr Asn
                500                 505                 510

Asn Cys Thr Pro Ala Cys Leu Pro Lys Asn Thr Lys Ile Ile Gly Pro
            515                 520                 525

Gly Lys Phe Asp Thr Asn Ala Glu Asp Gly Lys Ile Leu His Glu Met
530                 535                 540

Gly Gly His Leu Ser Glu Phe Leu Leu Leu Ser Leu Val Val Leu Ser
545                 550                 555                 560

Asp Phe Ala Pro Glu Thr Ala Ser Ala Leu Tyr Leu Ile Leu His Tyr
                565                 570                 575

Val Ile Pro Gln Ser His Glu Glu Pro Glu Gly Cys Asp Thr Asn Gln
                580                 585                 590

Leu Ala Leu Thr Val Glu Leu Arg Thr Glu Asp Val Ile Pro Ser Ser
                595                 600                 605

Val Trp Asn Val Gly Lys Tyr Val Cys Val Arg Pro Asp Trp Trp Pro
610                 615                 620

Tyr Glu Thr Lys Val Ala Leu Leu Phe Glu Glu Ala Gly Gln Val Val
625                 630                 635                 640

Lys Leu Ala Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
                660                 665                 670

Gln Val Val Gln Gly Val Ile Trp Leu Leu Leu Val Thr Gly Ala Gln
                675                 680                 685

Gly Arg Leu Ala Cys Lys Glu Asp His Arg Tyr Ala Ile Ser Thr Thr
            690                 695                 700

Asn Glu Ile Gly Leu Leu Gly Ala Glu Gly Leu Thr Thr Thr Trp Lys
705                 710                 715                 720

Glu Tyr Asn His Asn Leu Gln Leu Asp Asp Gly Thr Val Lys Ala Ile
                725                 730                 735

Cys Met Ala Gly Ser Phe Lys Val Thr Ala Leu Asn Val Val Ser Arg
                740                 745                 750

Arg Tyr Leu Ala Ser Leu His Lys Asp Ala Leu Pro Thr Ser Val Thr
            755                 760                 765

Phe Glu Leu Leu Phe Asp Gly Thr Ser Pro Leu Thr Glu Glu Met Gly
770                 775                 780
```

```
Asp Asp Phe Gly Phe Gly Leu Cys Pro Tyr Asp Thr Ser Pro Val Val
785                 790                 795                 800

Lys Gly Lys Tyr Asn Thr Thr Leu Leu Asn Gly Ser Ala Phe Tyr Leu
            805                 810                 815

Val Cys Pro Ile Gly Trp Thr Gly Val Ile Glu Cys Thr Ala Val Ser
        820                 825                 830

Pro Thr Thr Leu Arg Thr Glu Val Val Lys Thr Phe Arg Arg Glu Lys
            835                 840                 845

Pro Phe Pro Tyr Arg Arg Asp Cys Val Thr Thr Val Glu Asn Glu
850                 855                 860

Asp Leu Phe Tyr Cys Lys Trp Gly Gly Asn Trp Thr Cys Val Lys Gly
865                 870                 875                 880

Glu Pro Val Thr Tyr Thr Gly Gly Pro Val Lys Gln Cys Arg Trp Cys
                885                 890                 895

Gly Phe Asp Phe Asn Glu Pro Asp Gly Leu Pro His Tyr Pro Ile Gly
                900                 905                 910

Lys Cys Ile Leu Ala Asn Glu Thr Gly Tyr Arg Ile Val Asp Ser Thr
            915                 920                 925

Asp Cys Asn Arg Asp Gly Val Val Ile Ser Thr Glu Gly Ser His Glu
930                 935                 940

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Ala Gly
            965                 970                 975

Pro Val Arg Lys Thr Ser Cys Thr Phe Asn Tyr Ala Lys Thr Leu Arg
            980                 985                 990

Asn Arg Tyr Tyr Glu Pro Arg Asp Ser Tyr Phe Gln Gln Tyr Met Leu
            995                 1000                1005

Lys Gly Glu Tyr Gln Tyr Trp Phe Asp Leu Asp Val Thr Asp Arg
    1010                1015                1020

His Ser Asp Tyr Phe Ala Glu Phe Ile Val Leu Val Val Ala
    1025                1030                1035

Leu Leu Gly Gly Arg Tyr Val Leu Trp Leu Ile Val Thr Tyr Ile
    1040                1045                1050

Val Leu Thr Glu Gln Leu Ala Ala Gly Leu Gln Leu Gly Gln Gly
    1055                1060                1065

Glu Val Val Leu Ile Gly Asn Leu Ile Thr His Thr Asp Ile Glu
    1070                1075                1080

Val Val Val Tyr Phe Leu Leu Leu Tyr Leu Val Met Arg Asp Glu
    1085                1090                1095

Pro Ile Lys Lys Trp Ile Leu Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Lys Gly Gly Lys Ile Asp Gly Gly Trp Gln Arg Leu Pro
    1130                1135                1140

Glu Thr Asn Phe Asp Ile Gln Leu Ala Leu Thr Val Ile Val Val
    1145                1150                1155

Ala Val Met Leu Leu Ala Lys Lys Asp Pro Thr Thr Val Pro Leu
    1160                1165                1170

Val Ile Thr Val Ala Thr Leu Arg Thr Ala Lys Ile Thr Asn Gly
    1175                1180                1185

Leu Ser Thr Asp Leu Ala Ile Ala Thr Val Ser Thr Ala Leu Leu
    1190                1195                1200
```

-continued

Thr Trp Thr Tyr Ile Ser Asp Tyr Tyr Lys Tyr Lys Thr Leu Leu
1205                1210                1215

Gln Tyr Leu Ile Ser Thr Val Thr Gly Ile Phe Leu Ile Arg Val
1220                1225                1230

Leu Lys Gly Val Gly Glu Leu Asp Leu His Thr Pro Thr Leu Pro
1235                1240                1245

Ser Tyr Arg Pro Leu Phe Phe Ile Leu Val Tyr Leu Ile Ser Thr
1250                1255                1260

Ala Val Val Thr Arg Trp Asn Leu Asp Ile Ala Gly Leu Leu Leu
1265                1270                1275

Gln Cys Val Pro Thr Leu Leu Met Val Phe Thr Met Trp Ala Asp
1280                1285                1290

Ile Leu Thr Leu Ile Leu Ile Leu Pro Thr Tyr Glu Leu Thr Lys
1295                1300                1305

Leu Tyr Tyr Leu Lys Glu Val Lys Ile Gly Ala Glu Arg Gly Trp
1310                1315                1320

Leu Trp Lys Thr Asn Phe Lys Arg Val Asn Asp Ile Tyr Glu Val
1325                1330                1335

Asp Gln Ala Gly Glu Gly Val Tyr Leu Phe Pro Ser Lys Gln Lys
1340                1345                1350

Thr Gly Thr Ile Thr Gly Thr Met Leu Pro Leu Ile Lys Ala Ile
1355                1360                1365

Leu Ile Ser Cys Ile Ser Asn Lys Trp Gln Phe Ile Tyr Leu Leu
1370                1375                1380

Tyr Leu Ile Phe Glu Val Ser Tyr Tyr Leu His Lys Lys Ile Ile
1385                1390                1395

Asp Glu Ile Ala Gly Gly Thr Asn Phe Ile Ser Arg Leu Val Ala
1400                1405                1410

Ala Leu Ile Glu Ala Asn Trp Ala Phe Asp Asn Glu Glu Val Arg
1415                1420                1425

Gly Leu Lys Lys Phe Phe Leu Leu Ser Ser Arg Val Lys Glu Leu
1430                1435                1440

Ile Ile Lys His Lys Val Arg Asn Glu Val Met Val His Trp Phe
1445                1450                1455

Gly Asp Glu Glu Val Tyr Gly Met Pro Lys Leu Val Gly Leu Val
1460                1465                1470

Lys Ala Ala Thr Leu Ser Lys Asn Lys His Cys Ile Leu Cys Thr
1475                1480                1485

Val Cys Glu Asn Arg Glu Trp Arg Gly Glu Thr Cys Pro Lys Cys
1490                1495                1500

Gly Arg Phe Gly Pro Pro Val Thr Cys Gly Met Thr Leu Ala Asp
1505                1510                1515

Phe Glu Glu Lys His Tyr Lys Arg Ile Phe Phe Arg Glu Asp Gln
1520                1525                1530

Ser Glu Gly Pro Val Arg Glu Glu Tyr Ala Gly Tyr Leu Gln Tyr
1535                1540                1545

Arg Ala Arg Gly Gln Leu Phe Leu Arg Asn Leu Pro Val Leu Ala
1550                1555                1560

Thr Lys Val Lys Met Leu Leu Val Gly Asn Leu Gly Thr Glu Val
1565                1570                1575

Gly Asp Leu Glu His Leu Gly Trp Val Leu Arg Gly Pro Ala Val
1580                1585                1590

Cys Lys Lys Val Thr Glu His Glu Lys Cys Thr Thr Ser Ile Met

-continued

```
              1595                1600                1605

Asp Lys Leu Thr Ala Phe Phe Gly Val Met Pro Arg Gly Thr Thr
    1610                1615                1620

Pro Arg Ala Pro Val Arg Phe Pro Thr Ser Leu Leu Lys Ile Arg
    1625                1630                1635

Arg Gly Leu Glu Thr Gly Trp Ala Tyr Thr His Gln Gly Gly Ile
    1640                1645                1650

Ser Ser Val Asp His Val Thr Cys Gly Lys Asp Leu Leu Val Cys
    1655                1660                1665

Asp Thr Met Gly Arg Thr Arg Val Val Cys Gln Ser Asn Asn Lys
    1670                1675                1680

Met Thr Asp Glu Ser Glu Tyr Gly Val Lys Thr Asp Ser Gly Cys
    1685                1690                1695

Pro Glu Gly Ala Arg Cys Tyr Val Phe Asn Pro Glu Ala Val Asn
    1700                1705                1710

Ile Ser Gly Thr Lys Gly Ala Met Val His Leu Gln Lys Thr Gly
    1715                1720                1725

Gly Glu Phe Thr Cys Val Thr Ala Ser Gly Thr Pro Ala Phe Phe
    1730                1735                1740

Asp Leu Lys Asn Leu Lys Gly Trp Ser Gly Leu Pro Ile Phe Glu
    1745                1750                1755

Ala Ser Ser Gly Arg Val Val Gly Arg Val Lys Val Gly Lys Asn
    1760                1765                1770

Glu Asp Ser Lys Pro Thr Lys Leu Met Ser Gly Ile Gln Thr Val
    1775                1780                1785

Ser Lys Ser Thr Thr Asp Leu Thr Glu Met Val Lys Lys Ile Thr
    1790                1795                1800

Thr Met Asn Arg Gly Glu Phe Arg Gln Ile Thr Leu Ala Thr Gly
    1805                1810                1815

Ala Gly Lys Thr Thr Glu Leu Pro Arg Ser Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Gln Lys His Pro Ser Ile
    1850                1855                1860

Ala Phe Asn Leu Arg Ile Gly Glu Met Lys Glu Gly Asp Met Ala
    1865                1870                1875

Thr Gly Ile Thr Tyr Ala Ser Tyr Gly Tyr Phe Cys Gln Met Pro
    1880                1885                1890

Gln Pro Lys Leu Arg Ala Ala Met Val Glu Tyr Ser Phe Ile Phe
    1895                1900                1905

Leu Asp Glu Tyr His Cys Ala Thr Pro Glu Gln Leu Ala Ile Met
    1910                1915                1920

Gly Lys Ile His Arg Phe Ser Glu Asn Leu Arg Val Val Ala Met
    1925                1930                1935

Thr Ala Thr Pro Ala Gly Thr Val Thr Thr Thr Gly Gln Lys His
    1940                1945                1950

Pro Ile Glu Glu Tyr Ile Ala Pro Glu Val Met Lys Gly Glu Asp
    1955                1960                1965

Leu Gly Ser Glu Tyr Leu Asp Ile Ala Gly Leu Lys Ile Pro Val
    1970                1975                1980

Glu Glu Met Lys Ser Asn Met Leu Val Phe Val Pro Thr Arg Asn
    1985                1990                1995
```

-continued

```
Met Ala Val Glu Thr Ala Lys Lys Leu Lys Ala Lys Gly Tyr Asn
     2000                2005                2010

Ser Gly Tyr Tyr Tyr Ser Gly Glu Asp Pro Ser Asn Leu Arg Val
     2015                2020                2025

Val Thr Ser Gln Ser Pro Tyr Val Val Val Ala Thr Asn Ala Ile
     2030                2035                2040

Glu Ser Gly Val Thr Leu Pro Asp Leu Asp Val Val Val Asp Thr
     2045                2050                2055

Gly Leu Lys Cys Glu Lys Arg Ile Arg Leu Ser Pro Lys Met Pro
     2060                2065                2070

Phe Ile Val Thr Gly Leu Lys Arg Met Ala Val Thr Ile Gly Glu
     2075                2080                2085

Gln Ala Gln Arg Arg Gly Arg Val Gly Arg Val Lys Pro Gly Arg
     2090                2095                2100

Tyr Tyr Arg Ser Gln Glu Thr Pro Val Gly Ser Lys Asp Tyr His
     2105                2110                2115

Tyr Asp Leu Leu Gln Ala Gln Arg Tyr Gly Ile Glu Asp Gly Ile
     2120                2125                2130

Asn Ile Thr Lys Ser Phe Arg Glu Met Asn Tyr Asp Trp Ser Leu
     2135                2140                2145

Tyr Glu Glu Asp Ser Leu Met Ile Thr Gln Leu Glu Ile Leu Asn
     2150                2155                2160

Asn Leu Leu Ile Ser Glu Glu Leu Pro Met Ala Val Lys Asn Ile
     2165                2170                2175

Met Ala Arg Thr Asp His Pro Glu Pro Ile Gln Leu Ala Tyr Asn
     2180                2185                2190

Ser Tyr Glu Thr Gln Val Pro Val Leu Phe Pro Lys Ile Lys Asn
     2195                2200                2205

Gly Glu Val Thr Asp Ser Tyr Asp Asn Tyr Thr Phe Leu Asn Ala
     2210                2215                2220

Arg Lys Leu Gly Asp Asp Val Pro Pro Tyr Val Tyr Ala Thr Glu
     2225                2230                2235

Asp Glu Asp Leu Ala Val Glu Leu Leu Gly Leu Asp Trp Pro Asp
     2240                2245                2250

Pro Gly Asn Gln Gly Thr Val Glu Ala Gly Arg Ala Leu Lys Gln
     2255                2260                2265

Val Val Gly Leu Ser Thr Ala Glu Asn Ala Leu Leu Val Ala Leu
     2270                2275                2280

Phe Gly Tyr Val Gly Tyr Gln Ala Leu Ser Lys Arg His Ile Pro
     2285                2290                2295

Val Val Thr Asp Ile Tyr Ser Ile Glu Asp His Arg Leu Glu Asp
     2300                2305                2310

Thr Thr His Leu Gln Tyr Ala Pro Asn Ala Ile Lys Thr Glu Gly
     2315                2320                2325

Lys Glu Thr Glu Leu Lys Glu Leu Ala Gln Gly Asp Val Gln Arg
     2330                2335                2340

Cys Met Glu Ala Met Thr Asn Tyr Ala Arg Asp Gly Ile Gln Phe
     2345                2350                2355

Met Lys Ser Gln Ala Leu Lys Val Lys Glu Thr Pro Thr Tyr Lys
     2360                2365                2370

Glu Thr Met Asp Thr Val Ala Asp Tyr Val Lys Lys Phe Met Glu
     2375                2380                2385

Ala Leu Ala Asp Ser Lys Glu Asp Ile Ile Lys Tyr Gly Leu Trp
     2390                2395                2400
```

```
Gly Thr His Thr Thr Leu Tyr Lys Ser Ile Gly Ala Arg Leu Gly
    2405                2410                2415

Asn Glu Thr Ala Phe Ala Thr Leu Val Val Lys Trp Leu Ala Phe
    2420                2425                2430

Gly Gly Glu Ser Ile Ala Asp His Val Lys Gln Ala Ala Thr Asp
    2435                2440                2445

Leu Val Val Tyr Tyr Ile Ile Asn Arg Pro Gln Phe Pro Gly Asp
    2450                2455                2460

Thr Glu Thr Gln Gln Glu Gly Arg Lys Phe Val Ala Ser Leu Leu
    2465                2470                2475

Val Ser Ala Leu Ala Thr Tyr Thr Tyr Lys Ser Trp Asn Tyr Asn
    2480                2485                2490

Asn Leu Ser Lys Ile Val Glu Pro Ala Leu Ala Thr Leu Pro Tyr
    2495                2500                2505

Ala Ala Thr Ala Leu Lys Leu Phe Ala Pro Thr Arg Leu Glu Ser
    2510                2515                2520

Val Val Ile Leu Ser Thr Ala Ile Tyr Lys Thr Tyr Leu Ser Ile
    2525                2530                2535

Arg Arg Gly Lys Ser Asp Gly Leu Leu Gly Thr Gly Val Ser Ala
    2540                2545                2550

Ala Met Glu Ile Met Ser Gln Asn Pro Val Ser Val Gly Ile Ala
    2555                2560                2565

Val Met Leu Gly Val Gly Ala Val Ala Ala His Asn Ala Ile Glu
    2570                2575                2580

Ala Ser Glu Gln Lys Arg Thr Leu Leu Met Lys Val Phe Val Lys
    2585                2590                2595

Asn Phe Leu Asp Gln Ala Ala Thr Asp Glu Leu Val Lys Glu Ser
    2600                2605                2610

Pro Glu Lys Ile Ile Met Ala Leu Phe Glu Ala Val Gln Thr Val
    2615                2620                2625

Gly Asn Pro Leu Arg Leu Val Tyr His Leu Tyr Gly Val Phe Tyr
    2630                2635                2640

Lys Gly Trp Glu Ala Lys Glu Leu Ala Gln Arg Thr Ala Gly Arg
    2645                2650                2655

Asn Leu Phe Thr Leu Ile Met Phe Glu Ala Val Glu Leu Leu Gly
    2660                2665                2670

Val Asp Ser Glu Gly Lys Ile Arg Gln Leu Ser Ser Asn Tyr Ile
    2675                2680                2685

Leu Glu Leu Leu Tyr Lys Phe Arg Asp Ser Ile Lys Ser Ser Val
    2690                2695                2700

Arg Gln Met Ala Ile Ser Trp Ala Pro Ala Pro Phe Ser Cys Asp
    2705                2710                2715

Trp Thr Pro Thr Asp Asp Arg Ile Gly Leu Pro Gln Asp Asn Phe
    2720                2725                2730

Leu Arg Val Glu Thr Lys Cys Pro Cys Gly Tyr Lys Met Lys Ala
    2735                2740                2745

Val Lys Asn Cys Ala Gly Glu Leu Arg Leu Leu Glu Glu Glu Gly
    2750                2755                2760

Ser Phe Leu Cys Arg Asn Lys Phe Gly Arg Gly Ser Arg Asn Tyr
    2765                2770                2775

Arg Val Thr Lys Tyr Tyr Asp Asp Asn Leu Ser Glu Ile Lys Pro
    2780                2785                2790

Val Ile Arg Met Glu Gly His Val Glu Leu Tyr Tyr Lys Gly Ala
```

-continued

```
                    2795                2800                2805

Thr Ile Lys Leu Asp Phe Asn Asn Ser Lys Thr Ile Leu Ala Thr
        2810                2815                2820

Asp Lys Trp Glu Val Asp His Ser Thr Leu Val Arg Val Leu Lys
2825                2830                2835

Arg His Thr Gly Ala Gly Tyr Arg Gly Ala Tyr Leu Gly Glu Lys
    2840                2845                2850

Pro Asn His Lys His Leu Ile Glu Arg Asp Cys Ala Thr Ile Thr
        2855                2860                2865

Lys Asp Lys Val Cys Phe Leu Lys Met Lys Arg Gly Cys Ala Phe
2870                2875                2880

Thr Tyr Asp Leu Ser Leu His Asn Leu Thr Arg Leu Ile Glu Leu
    2885                2890                2895

Val His Lys Asn Asn Leu Glu Asp Lys Glu Ile Pro Ala Val Thr
2900                2905                2910

Val Thr Thr Trp Leu Ala Tyr Thr Phe Val Asn Glu Asp Ile Gly
    2915                2920                2925

Thr Ile Lys Pro Ala Phe Gly Glu Lys Ile Thr Pro Glu Met Gln
        2930                2935                2940

Glu Glu Ile Thr Leu Gln Pro Ala Val Val Asp Ala Thr Asp
2945                2950                2955

Val Thr Val Thr Val Val Gly Glu Thr Pro Thr Met Thr Thr Gly
    2960                2965                2970

Glu Thr Pro Thr Thr Phe Thr Ser Ser Gly Pro Asp Pro Lys Gly
        2975                2980                2985

Gln Gln Val Leu Lys Leu Gly Val Gly Glu Gly Gln Tyr Pro Gly
2990                2995                3000

Thr Asn Pro Gln Arg Ala Ser Leu His Glu Ala Ile Gln Ser Ala
    3005                3010                3015

Asp Glu Arg Pro Ser Val Leu Ile Leu Gly Ser Asp Lys Ala Thr
3020                3025                3030

Ser Asn Arg Val Lys Thr Val Lys Asn Val Lys Val Tyr Arg Gly
    3035                3040                3045

Arg Asp Pro Leu Glu Val Arg Asp Met Met Arg Arg Gly Lys Ile
3050                3055                3060

Leu Val Ile Ala Leu Ser Arg Val Asp Asn Ala Leu Leu Lys Phe
    3065                3070                3075

Val Asp Tyr Lys Gly Thr Phe Leu Thr Arg Glu Thr Leu Glu Ala
3080                3085                3090

Leu Ser Leu Gly Arg Pro Lys Lys Lys Asn Ile Thr Lys Ala Glu
    3095                3100                3105

Ala Gln Trp Leu Leu Arg Leu Glu Asp Gln Met Glu Glu Leu Pro
3110                3115                3120

Asp Trp Phe Ala Ala Gly Glu Pro Ile Phe Leu Glu Ala Asn Ile
    3125                3130                3135

Lys His Asp Arg Tyr His Leu Val Gly Asp Ile Ala Thr Ile Lys
3140                3145                3150

Glu Lys Ala Lys Gln Leu Gly Ala Thr Asp Ser Thr Lys Ile Ser
    3155                3160                3165

Lys Glu Val Gly Ala Lys Val Tyr Ser Met Lys Leu Ser Asn Trp
        3170                3175                3180

Val Met Gln Glu Glu Asn Lys Gln Ser Asn Leu Thr Pro Leu Phe
    3185                3190                3195
```

-continued

Glu Glu Leu Leu Gln Gln Cys Pro Pro Gly Gly Gln Asn Lys Thr
3200             3205                 3210

Ala His Met Val Ser Ala Tyr Gln Leu Ala Gln Gly Asn Trp Met
3215             3220                 3225

Pro Thr Ser Cys His Val Phe Met Gly Thr Ile Ser Ala Arg Arg
3230             3235                 3240

Thr Lys Thr His Pro Tyr Glu Ala Tyr Val Lys Leu Arg Glu Leu
3245             3250                 3255

Val Glu Glu His Lys Met Lys Thr Leu Cys Pro Gly Ser Ser Leu
3260             3265                 3270

Arg Lys His Asn Glu Trp Val Ile Gly Lys Ile Lys Tyr Gln Gly
3275             3280                 3285

Asn Leu Arg Thr Lys His Met Leu Asn Pro Gly Lys Val Ala Glu
3290             3295                 3300

Gln Leu His Arg Glu Gly His Arg His Asn Val Tyr Asn Lys Thr
3305             3310                 3315

Ile Gly Ser Val Met Thr Ala Thr Gly Ile Arg Leu Glu Lys Leu
3320             3325                 3330

Pro Val Val Arg Ala Gln Thr Asp Thr Thr Asn Phe His Gln Ala
3335             3340                 3345

Ile Arg Asp Lys Ile Asp Lys Glu Glu Asn Leu Gln Thr Pro Gly
3350             3355                 3360

Leu His Lys Lys Leu Met Glu Val Phe Asn Ala Leu Lys Arg Pro
3365             3370                 3375

Glu Leu Glu Ser Ser Tyr Asp Ala Val Glu Trp Glu Glu Leu Glu
3380             3385                 3390

Arg Gly Ile Asn Arg Lys Gly Ala Ala Gly Phe Phe Glu Arg Lys
3395             3400                 3405

Asn Ile Gly Glu Ile Leu Asp Ser Glu Lys Asn Lys Val Glu Glu
3410             3415                 3420

Ile Ile Asp Asn Leu Lys Lys Gly Arg Asn Ile Lys Tyr Tyr Glu
3425             3430                 3435

Thr Ala Ile Pro Lys Asn Glu Lys Arg Asp Val Asn Asp Asp Trp
3440             3445                 3450

Thr Ala Gly Asp Phe Val Asp Glu Lys Lys Pro Arg Val Ile Gln
3455             3460                 3465

Tyr Pro Glu Ala Lys Thr Arg Leu Ala Ile Thr Lys Val Met Tyr
3470             3475                 3480

Lys Trp Val Lys Gln Lys Pro Val Val Ile Pro Gly Tyr Glu Gly
3485             3490                 3495

Lys Thr Pro Leu Phe Gln Ile Phe Asp Lys Val Lys Lys Glu Trp
3500             3505                 3510

Asp Gln Phe Gln Asn Pro Val Ala Val Ser Phe Asp Thr Lys Ala
3515             3520                 3525

Trp Asp Thr Gln Val Thr Thr Asn Asp Leu Glu Leu Ile Lys Asp
3530             3535                 3540

Ile Gln Lys Tyr Tyr Phe Lys Lys Lys Trp His Lys Phe Ile Asp
3545             3550                 3555

Thr Leu Thr Met His Met Ser Glu Val Pro Val Ile Thr Ala Asp
3560             3565                 3570

Gly Glu Val Tyr Ile Arg Lys Gly Gln Arg Gly Ser Gly Gln Pro
3575             3580                 3585

Asp Thr Ser Ala Gly Asn Ser Met Leu Asn Val Leu Thr Met Val
3590             3595                 3600

Tyr Ala Phe Cys Glu Ala Gly Val Pro Tyr Lys Ser Phe Asp
3605                3610                3615

Arg Val Ala Lys Ile His Val Cys Gly Asp Asp Gly Phe Leu Ile
3620                3625                3630

Thr Glu Arg Ala Leu Gly Glu Lys Phe Ala Ser Lys Gly Val Gln
3635                3640                3645

Ile Leu Tyr Glu Ala Gly Lys Pro Gln Lys Ile Thr Glu Gly Asp
3650                3655                3660

Lys Met Lys Val Ala Tyr Gln Phe Asp Asp Ile Glu Phe Cys Ser
3665                3670                3675

His Thr Pro Ile Gln Val Arg Trp Ser Asp Asn Thr Ser Ser Tyr
3680                3685                3690

Met Pro Gly Arg Asn Thr Thr Thr Ile Leu Ala Lys Met Ala Thr
3695                3700                3705

Arg Leu Asp Ser Ser Gly Glu Arg Gly Thr Ile Ala Tyr Glu Lys
3710                3715                3720

Ala Val Ala Phe Ser Phe Leu Leu Met Tyr Ser Trp Asn Pro Leu
3725                3730                3735

Ile Arg Arg Ile Cys Leu Leu Val Leu Ser Thr Glu Leu Gln Val
3740                3745                3750

Lys Pro Gly Lys Ser Thr Thr Tyr Tyr Tyr Glu Gly Asp Pro Ile
3755                3760                3765

Ser Ala Tyr Lys Glu Val Ile Gly His Asn Leu Phe Asp Leu Lys
3770                3775                3780

Arg Thr Ser Phe Glu Lys Leu Ala Lys Leu Asn Leu Ser Met Ser
3785                3790                3795

Val Leu Gly Ala Trp Thr Arg His Thr Ser Lys Arg Leu Leu Gln
3800                3805                3810

Asp Cys Val Asn Met Gly Val Lys Glu Gly Asn Trp Leu Val Asn
3815                3820                3825

Ala Asp Arg Leu Val Ser Ser Lys Thr Gly Asn Arg Tyr Val Pro
3830                3835                3840

Gly Glu Gly His Thr Leu Gln Gly Arg His Tyr Glu Glu Leu Val
3845                3850                3855

Leu Ala Arg Lys Gln Ile Asn Ser Phe Gln Gly Thr Asp Arg Tyr
3860                3865                3870

Asn Leu Gly Pro Ile Val Asn Met Val Leu Arg Arg Leu Arg Val
3875                3880                3885

Met Met Met Thr Leu Ile Gly Arg Gly Val
3890                3895

<210> SEQ ID NO 5
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 5
tatgccctat caccttattg tgctgtgaca agcaaaatag ggtac        45

<210> SEQ ID NO 6
<211> LENGTH: 45
<212> TYPE: DNA
<213> ORGANISM: Artificial Sequence
<220> FEATURE:
<223> OTHER INFORMATION: Chemically Synthesized -continued

<400> SEQUENCE: 6
gggtacatat ggtacactaa cgcctgtacc ccggcttgcc tcccc                    45

<210> SEQ ID NO 7
<211> LENGTH: 48
<212> TYPE: DNA
<213> ORGANISM: Artificial Sequence
<220> FEATURE:
<223> OTHER INFORMATION: Chemically Synthesized

<400> SEQUENCE: 7
gaaggctgtg acacaaacca gctggcttta acagtggaac tcaggact              48

<210> SEQ ID NO 8
<211> LENGTH: 4
<212> TYPE: PRT
<213> ORGANISM: Classical Swine Fever Virus

<400> SEQUENCE: 8

Asn Val Thr Ser
1

<210> SEQ ID NO 9
<211> LENGTH: 4
<212> TYPE: PRT
<213> ORGANISM: Classical Swine Fever Virus

<400> SEQUENCE: 9

Ala Val Thr Ser
1

<210> SEQ ID NO 10
<211> LENGTH: 4
<212> TYPE: PRT
<213> ORGANISM: Classical Swine Fever Virus

<400> SEQUENCE: 10

Asn Cys Thr Pro
1

<210> SEQ ID NO 11
<211> LENGTH: 4
<212> TYPE: PRT
<213> ORGANISM: Classical Swine Fever Virus

<400> SEQUENCE: 11

Ala Cys Thr Pro
1

<210> SEQ ID NO 12
<211> LENGTH: 4
<212> TYPE: PRT
<213> ORGANISM: Classical Swine Fever Virus

<400> SEQUENCE: 12

Asn Leu Thr Val
1

<210> SEQ ID NO 13
<211> LENGTH: 4
<212> TYPE: PRT
<213> ORGANISM: Classical Swine Fever Virus

```
<400> SEQUENCE: 13

Ala Leu Thr Val
1
```